(12) United States Patent
Tanaka et al.

(10) Patent No.: US 9,174,918 B2
(45) Date of Patent: Nov. 3, 2015

(54) PROCESS FOR PREPARING DIARYL OXALATE

(75) Inventors: Shuji Tanaka, Ube (JP); Hirofumi Ii, Ube (JP)

(73) Assignee: UBE INDUSTRIES, LTD., Ube-shi (JP)

(*) Notice: Subject to any disclaimer, the term of this patent is extended or adjusted under 35 U.S.C. 154(b) by 70 days.

(21) Appl. No.: 13/522,979

(22) PCT Filed: Jan. 20, 2011

(86) PCT No.: PCT/JP2011/051015
§ 371 (c)(1),
(2), (4) Date: Jul. 19, 2012

(87) PCT Pub. No.: WO2011/090138
PCT Pub. Date: Jul. 28, 2011

(65) Prior Publication Data
US 2012/0296063 A1  Nov. 22, 2012

(30) Foreign Application Priority Data

| Jan. 20, 2010 | (JP) | 2010-009651 |
| Jan. 20, 2010 | (JP) | 2010-009652 |
| Jan. 20, 2010 | (JP) | 2010-009653 |
| Jan. 20, 2010 | (JP) | 2010-009654 |

(51) Int. Cl.
C07C 67/02 (2006.01)
C07C 67/03 (2006.01)
C07C 68/00 (2006.01)
C08G 64/30 (2006.01)

(52) U.S. Cl.
CPC ............ *C07C 67/03* (2013.01); *C07C 68/00* (2013.01); *C08G 64/307* (2013.01)

(58) Field of Classification Search
CPC .... B01J 2531/46; B01J 31/0214; B01J 37/00; C08L 67/02
USPC .................................................. 560/92, 99
See application file for complete search history.

(56) References Cited

U.S. PATENT DOCUMENTS

| 5,731,453 A | 3/1998 | Nishihira et al. |
| 5,811,573 A | 9/1998 | Nishihira et al. |
| 5,834,615 A * | 11/1998 | Nishihira et al. ............ 558/274 |
| 6,018,072 A * | 1/2000 | Nishihira et al. ............ 560/146 |
| 6,740,729 B1 * | 5/2004 | Tanaka et al. ................ 528/196 |

FOREIGN PATENT DOCUMENTS

| JP | 9-143123 A | 6/1997 |
| JP | 9-301920 A | 11/1997 |
| JP | 10-59905 A | 3/1998 |
| JP | 10-158216 A | 6/1998 |
| JP | 11-246490 A | 9/1999 |
| JP | 2000-072721 * | 3/2000 ............ C07C 69/96 |
| JP | 2006-89417 A | 4/2006 |

OTHER PUBLICATIONS

International Preliminary Report on Patentability for International Patent Application No. PCT/JP2011/051015, dated Aug. 16, 2012.
International Search Report issued in PCT/JP2011/051015, mailed on Mar. 8, 2011.

* cited by examiner

*Primary Examiner* — Sudhakar Katakam
*Assistant Examiner* — Pancham Bakshi
(74) *Attorney, Agent, or Firm* — Birch, Stewart, Kolasch & Birch, LLP

(57) ABSTRACT

Disclosed is a process for preparing a diaryl oxalate which comprises the step of transesterifying a dialkyl oxalate or/and an alkylaryl oxalate with an aryl alcohol in the presence of a tetra(aryloxy)titanium as a catalyst, wherein the tetra(aryloxy)titanium is fed into a reaction system of the transesterification as an aryl alcohol solution of the tetra(aryloxy)titanium which is prepared by reacting a tetraalkoxy titanium and an excess amount of the aryl alcohol and removing a by-producing alkyl alcohol.

15 Claims, No Drawings

US 9,174,918 B2

PROCESS FOR PREPARING DIARYL OXALATE

TECHNICAL FIELD

The present invention relates to a process for preparing a diaryl oxalate by subjecting a dialkyl oxalate or/and an alkylaryl oxalate with an aryl alcohol to transesterification.

BACKGROUND ART

The diaryl oxalate is useful for a starting material of a diaryl carbonate by decarbonylation, which has widely been used as a monomer for preparing a polycarbonate by the melting method, and is a compound having attracted attention in recent years. The diaryl oxalate can be prepared by transesterification of a dialkyl oxalate and an aryl alcohol, and the dialkyl oxalate to be used can be prepared from carbon monoxide and an alkyl nitrite.

It has been proposed a sequential process for preparing a diaryl carbonate from carbon monoxide and an alkyl nitrite through a dialkyl oxalate and a diaryl oxalate (see Patent Literature 1).

It has also been proposed a process for preparing a diaryl oxalate which comprises transesterifying a dialkyl oxalate and an aryl alcohol in the presence of a transesterification catalyst, to form an alkylaryl oxalate as an intermediate while removing a by-producing alkyl alcohol by distillation, then, subjecting the alkylaryl oxalate to disproportionation reaction in the presence of a catalyst to form a diaryl oxalate while removing an unreacted dialkyl oxalate by distillation, and recovering the diaryl oxalate by distillating the reaction mixture (see Patent Literature 2).

Further, as a catalyst to be used for preparing a diaryl oxalate by transesterifying a dialkyl oxalate and an aryl alcohol in the presence of a catalyst, it has been proposed to use a titanium compound, a tin compound, a lead compound, a zirconium compound, a molybdenum compound and a ytterbium compound, and among these, a titanium compound has been most preferably used (see Patent Literature 3).

Examples of the titanium compound may be mentioned $TiX_3$, $Ti(OAc)_3$, $Ti(OMe)_3$, $Ti(OEt)_3$, $Ti(OBu)_3$, $Ti(OPh)_3$, $TiX_4$, $Ti(OAc)_4$, $Ti(OMe)_4$, $Ti(OEt)_4$, $Ti(OBu)_4$, $Ti(OPh)_4$ (wherein Ac represents an acetyl group, Me represents a methyl group, Et represents an ethyl group, Bu represents a butyl group, Ph represents a phenyl group, and X represents a halogen atom), and in particular, $Ti(OPh)_4$ [tetra(phenoxy)titanium] is preferred as a catalyst showing excellent transesterification ability.

However, a tetra(aryloxy)titanium such as tetraphenoxy titanium, etc., easily decomposes by reacting with a minute amount of water. Also, the tetra(aryloxy)-titanium is in a solid state at normal temperature, and complicated operations such as solid-liquid separation, etc., are required for purifying the same.

Moreover, it is difficult to use the solid state tetra(aryloxy) titanium for a continuous preparation process of the diaryl oxalate, so that the tetra(aryloxy)titanium is required to be in a liquid state by melting it with heat or dissolving it in a solvent. However, the tetra(aryloxy)titanium is sparingly soluble in the dialkyl oxalate, and has less solubility in an aryl alcohol, which causes increase in a number of processing apparatuses, whereby there is a problem that the preparation steps of the diaryl oxalate are complicated.

The diaryl oxalate obtained by the above-mentioned preparation method, etc., becomes a diaryl carbonate by decarbonylation, and as a final use, it becomes a starting material for a polycarbonate by the melt polycondensation with a bisaryl alcohol A.

The polycarbonate has widely been used for a disc such as CD and DVD, and a plastic lens as an engineering plastic having high transparency. Therefore, to heighten transparency of the resin, it is required not to contain any coloring component for the diaryl carbonate which is a starting material of the polycarbonate, and further for the diaryl oxalate which is a starting material of the diaryl carbonate.

Also, in the above-mentioned preparation method, the reaction and purification by separation are carried out by using a plural steps of a distillation column, but according to the investigation of the preparation method by the present inventors, it was found that corrosion or thinned-down of material was observed at the portion contacting with a reaction mixture, such as the distillation column, storage tank, piping, etc., which are made of an austenitic stainless steel such as SUS304 regulated by JIS G 4304 and generally used for a material of an apparatus such as the distillation column, etc., whereas no compound containing a halogen atom is contained in the reaction mixture, whereby the preparation for a long period of time was difficult.

Furthermore, in the alkyl alcohol removed by the distillation according to the above-mentioned preparation method, impurities with a low boiling point formed at the time of the transesterification are contained, and when they are recycled into the dialkyl oxalate preparation step, unfavorable states that lowering in yield or selectivity of the forming reaction or increase in formed impurities are caused.

PRIOR ART LITERATURES

Patent Literature

[Patent Literature 1] JP H11-246490A
[Patent Literature 2] JP H09-301920A
[Patent Literature 3] JP 2006-089417A

DISCLOSURE OF THE INVENTION

Problems to be Solved by the Invention

An object of the present invention is to solve the above-mentioned problems, and is to provide a process for preparing a diaryl oxalate which comprises feeding a tetra(aryloxy) titanium into a reaction system of transesterification effectively, which is advantageous to carry out a process for preparing a diaryl oxalate by transesterification of a dialkyl oxalate or/and an alkylaryl oxalate with an aryl alcohol industrially.

An object of the present invention is to provide a process for preparing a diaryl oxalate or the diaryl oxalate which can prepare a high purity diaryl carbonate containing no coloring component, for preparing a diaryl carbonate by decarbonylating the diaryl oxalate prepared by the above-mentioned process.

An object of the present invention is to provide a process for preparing a diaryl oxalate by using an apparatus which difficultly causes corrosion or material wastage when a dialkyl oxalate or/and an alkylaryl oxalate is/are transesterified with an aryl alcohol, and can be used for a long period of time industrially.

An object of the present invention is to provide a process for preparing a diaryl oxalate which is industrially advantageous and effective for preparing the diaryl carbonate through a dialkyl oxalate and a diaryl oxalate using carbon monoxide, oxygen and an alkyl alcohol as starting materials. In particular, this is to provide a process for preparing a diaryl oxalate which is used for preparing a diaryl carbonate, by reducing lowering in reaction yield or selectivity of the dialkyl oxalate, which are specific problems in transesterifying an aryl alcohol having a phenolic hydroxyl group and a dialkyl oxalate.

Means to Solve the Problems

The present inventors have earnestly studied to solve the above above-mentioned problems, and as a result, they have obtained the following findings to accomplish the present invention.

The present inventors have obtained the finding that a tetraalkoxy titanium and an excess amount of the aryl alcohol are reacted under specific conditions, and a by-producing alkyl alcohol is removed, an aryl alcohol solution of the tetra(aryloxy)-titanium can be formed. Also, the present inventors have obtained the finding that the tetra(aryloxy) titanium which is an objective material is fed without isolating and purifying from the solution to the step of transesterifying a dialkyl oxalate or/and an alkylaryl oxalate, with an aryl alcohol as such, a diaryl oxalate can be prepared effectively.

The present inventors have obtained the finding that, in the above-mentioned method, purification by distillation is carried out so that a concentration of the titanium compound in the reaction mixture obtained by transesterification is made a specific value or less, a diaryl oxalate with a less coloring degree can be prepared, to accomplish the present invention. That is, the present inventors have earnestly studied to solve the above-mentioned problems, and as a result, they have found that one of coloring components contained in the diaryl oxalate to be used as a starting material when the diaryl carbonate is prepared by decarbonylation of a diaryl oxalate is a furan compound, and by controlling a content of the furan compound to a specific amount or less, a diaryl oxalate with a less coloring degree can be obtained, to accomplish the present invention.

The present inventors have obtained the finding that, in the above-mentioned method, a material of an apparatus contacting with a reaction solution of the trans-esterification is an austenitic stainless steel containing 10% by weight or more of nickel, and 1 to 4% by weight of molybdenum, corrosion or material wastage can be controlled, and preparation can be continued for a long period of time continuously, to accomplish the present invention.

The present inventors have obtained the finding that, in the above-mentioned method, a dialkyl oxalate is firstly prepared by using carbon monoxide, oxygen and an alkyl alcohol as starting materials, and when the dialkyl oxalate or/and an alkylaryl oxalate, and an aryl alcohol are transesterified, an amount of the ether compound contained in a by-producing alkyl alcohol is made a specific amount or less and recycled it into a dialkyl oxalate step, whereby it is industrially advantageous and effectively prepared, to accomplish the present invention.

That is, the present invention specifically has the following constitutions.

(1) A process for preparing a diaryl oxalate which comprises
a step of transesterifying a dialkyl oxalate or/and an alkylaryl oxalate, with an aryl alcohol in the presence of a tetra(aryloxy)titanium as a catalyst,
wherein the tetra(aryloxy)titanium is fed in a reaction system of transesterification as an aryl alcohol solution of the tetra(aryloxy)titanium which is obtained by reacting a tetraalkoxy titanium and an excess amount of an aryl alcohol and removing a by-producing alkyl alcohol.

(2) The process for preparing diaryl oxalate of the above-mentioned (1), wherein the process further comprises a step of making a concentration of a titanium compound of a reaction mixture containing the diaryl oxalate 10 ppm by weight or less, and then, purifying by distillation.

(3) The process for preparing diaryl oxalate of the above-mentioned (1), wherein a material of an apparatus contacting with a reaction solution of the transesterification is an austenitic stainless steel containing 10% by weight or more of nickel, and 1 to 4% by weight of molybdenum.

(4) The process for preparing diaryl oxalate of the above-mentioned (1), which comprises
Step (A) of reacting carbon monoxide, oxygen and an alkyl alcohol to prepare a dialkyl oxalate,
Step (B-1) of reacting the dialkyl oxalate obtained in Step (A) and an aryl alcohol in the presence of an aryl alcohol solution of the tetra(aryloxy)titanium to form an alkylaryl oxalate while removing a forming alkyl alcohol,
Step (B-2) of subjecting disproportionation of the alkylaryl oxalate obtained in Step (B-1) in the presence of an aryl alcohol solution of the tetra(aryloxy)titanium, to form a diaryl oxalate while removing a forming dialkyl oxalate and alkyl alcohol, and
Step (B-3) of separating and recovering the diaryl oxalate obtained in Step (B-2), and further comprises
Step (C) of making a content of the ether compound in the alkyl alcohol removed in Step (B-1) less than 1000 ppm by weight, and recycling the alkyl alcohol into Step (A).

(5) The process for preparing diaryl oxalate of the above-mentioned any one of (1) to (4), wherein the tetra(aryloxy) titanium is tetraphenoxy titanium.

(6) The process for preparing diaryl oxalate of the above-mentioned any one of (1) to (5), wherein the tetraalkoxy titanium is tetraisopropoxy titanium.

(7) The process for preparing diaryl oxalate of the above-mentioned any one of (1) to (6), wherein the reaction of the tetraalkoxy titanium and an excess amount of the aryl alcohol is carried out so that a molar ratio (aryl alcohol/titanium atom) of the aryl alcohol and a titanium atom in the tetraalkoxy titanium becomes 10 to 80.

(8) The process for preparing diaryl oxalate of the above-mentioned any one of (1) to (7), wherein the reaction of the tetraalkoxy titanium and an excess amount of the aryl alcohol is carried out while maintaining a reaction temperature at 160 to 300° C.

(9) The process for preparing diaryl oxalate of the above-mentioned any one of (1) to (8), wherein the reaction of the tetraalkoxy titanium and an excess amount of the aryl alcohol is carried out in a reaction-distillation column.

(10) The process for preparing diaryl oxalate of the above-mentioned (9), wherein a reflux ratio of the tetraalkoxy titanium and an excess amount of the aryl alcohol in the reaction-distillation column is 3 to 40.

(11) The process for preparing diaryl oxalate of the above-mentioned (9) or (10), wherein the tetraalkoxy titanium and an excess amount of the aryl alcohol are continuously fed to the reaction-distillation column so that a molar ratio (aryl alcohol/titanium atom) of the aryl alcohol and a titanium atom in the tetraalkoxy titanium per a unit time becomes 40 to 80.

(12) The process for preparing diaryl oxalate of the above-mentioned any one of (1) to (11), wherein the tetraalkoxy titanium and an excess amount of the aryl alcohol are fed to a reaction-distillation column to carry out a reaction, a fraction containing a by-producing alkyl alcohol is taken out by distillation, and a fraction containing the tetra-(aryloxy)titanium and the aryl alcohol is taken out from a bottom portion, to obtain an aryl alcohol solution of the tetra(aryloxy)titanium from which the by-producing alkyl alcohol had been removed, and fed the same to a transesterification step.

(13) The process for preparing diaryl oxalate of the above-mentioned (12), wherein the tetra(aryloxy)titanium and the aryl alcohol are continuously taken out from a bottom portion of the reaction-distillation column, and the aryl alcohol solution of the tetra-(aryloxy)titanium from which the by-producing alkyl alcohol had been removed is continuously fed to the transesterification step.

(14) The process for preparing diaryl oxalate of the above-mentioned any one of (1) to (13), wherein a material of an apparatus contacting with a reaction solution of the transesterification is an austenitic stainless steel containing 16.00 to 18.00% by weight of chromium.

(15) The process for preparing diaryl oxalate of the above-mentioned (14), wherein the material of an apparatus is an austenitic stainless steel substantially not containing a nitrogen atom.

(16) The process for preparing diaryl oxalate of the above-mentioned (15), wherein a material of an apparatus is a SUS316 series austenitic stainless steel regulated by JIS G 4304.

(17) The process for preparing diaryl oxalate of the above-mentioned (16), wherein the austenitic stainless steel is SUS316 or SUS316L regulated by JIS G 4304.

(18) The process for preparing diaryl oxalate of the above-mentioned any one of (1) to (17), wherein an apparatus is a purification column of the diaryl oxalate, a reaction apparatus of transesterification or a reaction-distillation column.

(19) The process for preparing diaryl oxalate of the above-mentioned (4), wherein a content of an ether compound in the alkyl alcohol is made 300 ppm by weight or lower in Step (C).

(20) The process for preparing diaryl oxalate of the above-mentioned (4) or (19), wherein the ether compound in Step (C) is an alkyl aryl ether.

(21) The process for preparing diaryl oxalate of the above-mentioned (4), (19) or (20), wherein a compound in which an oxalate having at least one aryl ester group or a decomposed product thereof is subjected to Fries rearrangement, and a compound having a hydroxy group and an aryloxy group, or a compound in which the hydroxy group and the aryloxy group of the above compound is intermolecularly or intramolecularly reacted, or a derivative thereof is removed in Step (B-3).

(22) A process for preparing diaryl carbonate which comprises decarbonylating the diaryl oxalate prepared by the process of the above-mentioned any one of (1) to (21) in the presence of a phosphorus compound.

(23) A process for preparing polycarbonate which comprises reacting diaryl carbonate prepared by the process of the above-mentioned (22) with bisphenol A in the presence of a basic alkali metal salt.

Effects of the Invention

According to the preparation process of a diaryl oxalate of the present invention, an aryl alcohol solution of the tetra (aryloxy)titanium to be used as a catalyst can be prepared with a high conversion by reacting a tetraalkoxy titanium and an excess amount of an aryl alcohol under specific conditions.

Also, the formed tetra(aryloxy)titanium can be fed as an aryl alcohol solution as such to the step of subjecting to transesterification of a dialkyl oxalate or/and alkylaryl oxalate with an aryl alcohol, so that the purification step can be markedly simplified and omitted. In addition, preparation facilities can be simplified and omitted, and a solvent for purification can be reduced whereby a load to environment can be reduced. Also, according to simplification of the steps, a detention time, thermal history against tetra(aryloxy)titanium, deterioration of water, etc., and contact with decomposed substances are reduced, and decomposed products can be controlled whereby selectivity of the diaryl oxalate and reaction efficiency can be improved.

According to the preparation process of a diaryl oxalate of the present invention, a highly non-coloring diaryl oxalate which contains no coloring component causing reddish or yellow tint can be obtained by controlling a content of a furan compound with a specific amount or less, and by decarbonylating the same, a highly non-coloring diaryl carbonate can be prepared. The diaryl oxalate obtained by the present invention is extremely useful as a starting material particularly for a poly-oxamide resin, etc., to be used for an optical material such as an optical lens and an optical filter, and a diaryl carbonate obtained from the diaryl oxalate is also extremely useful as a starting material of the polycarbonate resin similarly used for an optical material.

According to the preparation process of a diaryl oxalate of the present invention, corrosion or material wastage at the portion with which the reaction mixture contacts can be controlled so that repairment or replacement of a contacting portion with the mixture such as a distillation column, tanks, pipings, etc., is not necessary for a long period of time whereby it is industrially extremenly advantageous. Also, there is no fear of liquid leakage caused by corrosion so that improvement in safety can be also expected. As a result, a diaryl carbonate which is to be prepared by using a diaryl oxalate as a starting material can be industrially advantageously and stably produced in the points of costs, etc.

According to the preparation process of a diaryl oxalate of the present invention, a dialkyl oxalate or/and alkylaryl oxalate and an aryl alcohol are subjected to transesterification, and when a formed alkyl alcohol is recycled into the preparation step of the dialkyl oxalate, the dialkyl oxalate can be prepared with high yield and high selectivity.

BEST MODE TO CARRY OUT THE INVENTION

Explanation of the constitutional elements mentioned below is one example (representative example) of the embodiments of the present invention, and the present invention is not limited by these.

[Dialkyl Oxalate]

The dialkyl oxalate to he used in the present invention is not particularly limited, and two alkyl groups in the dialkyl oxalate molecule may be the same or different from each other. The dialkyl oxalate that may be used includes, for example, a dialkyl oxalate such as dimethyl oxalate, diethyl oxalate, dipropyl oxalate, diisopropyl oxalate, dibutyl oxalate, dipentyl oxalate, dihexyl oxalate, diheptyl oxalate, dioctyl oxalate, dinonyl oxalate, etc. Among the dialkyl oxalates, a dialkyl oxalate having linear or branched alkyl groups with 1 to 10 carbon atoms is preferred in the viewponts of a reaction rate of transesterification and easiness in removing a by-producing alkyl alcohol, and dimethyl oxalate or diethyl oxalate is particularly preferred.

[Preparation Process of Dialkyl Oxalate]

A preparation process of a dialkyl oxalate to be used in the present invention is not particularly limited, and a material prepared by any of the processes may be used. In the following, Step (A) for preparing the dialkyl oxalate to be used in the present invention is explained. Step (A) is a step for preparing the dialkyl oxalate by reacting carbon monoxide, oxygen and an alkyl alcohol.

[Step (A)]

In this step, in addition to an alkyl alcohol and oxygen to be used as starting materials, nitrogen monoxide is reacted to form an alkyl nitrite, and the product is further reacted with carbon monoxide to form a dialkyl oxalate. As a catalyst to react the alkyl nitrite and the carbon monoxide, a platinum group metal catalyst is suitably used. The platinum group metal catalyst may be mentioned a platinum group metal or a compound thereof, and the platinum group metal compound is preferably used in the form of a platinum group metal by reducing the same.

The platinum group metal that may be used includes, for example, platinum metal, palladium metal, rhodium metal, iridium metal, etc., and the compound thereof that may be used includes, for example, an inorganic acid salt (a nitrate, a sulfate, a phosphate, etc.), a halide (a chloride, a bromide, etc.), an organic acid salt (an acetate, an oxalate, a benzoate, etc.), a complex, etc., of these metals. Among the platinum group metal or a compound thereof, palladium metal or a compound thereof is particularly preferred.

The palladium compound that may be used includes, for example, an inorganic acid salt of palladium (palladium nitrate, palladium sulfate, palladium phosphate, etc.), a halide of palladium (palladium chloride, palladium bromide, etc.), an organic acid salt of palladium (palladium acetate, palladium oxalate, palladium benzoate, etc.), or a complex of palladium (a complex having an alkylphosphine such as trimethylphosphine, etc., an arylphosphine such as triphenylphosphine, etc., an alkylphenylphosphine such as diethylphenylphosphine, etc., or an arylphosphite such as triphenylphosphite, etc., as a ligand(s)), etc.

The platinum group metal catalyst is preferably used as a solid catalyst industrially in which a platinum group metal or its compound is carried on an inactive carrier, calculated in terms of a platinum group metal, preferably in an amount of 0.01 to 10% by weight, more preferably 0.2 to 2% by weight. The inactive carrier that may be mentioned includes, for example, activated charcoal, alumina (a-alumina, etc.), silica, diatomaceous earth, pumice stone, zeolite, Molecular Sieve, spinel, etc. When the solid catalyst in which a platinum group metal compound is carried on a carrier is to be used, it is preferred that the carried platinum group metal compound is previously reduced to a platinum group metal by using a reductive substance such as hydrogen, etc., and then, used, or before the reaction, it is reduced to a platinum group metal by a reductive substance such as carbon monoxide, etc., in the reactor, and then, used. The platinum group metal catalyst is carried on a carrier by the well-known method (the impregnation method, evaporation to dryness method, etc.).

In the platinum group metal catalyst, for example, iron or its compound may be contained. Iron or its compound may be mentioned a metal iron, an iron(II) compound or an iron(III) compound. The iron(II) compound that may be preferably used includes, for example, ferrous sulfate, ferrous nitrate, ferrous chloride, ferrous ammonium sulfate, ferrous lactate, ferrous hydroxide, etc., and the iron(III) compound that may be preferably used includes ferric sulfate, ferric nitrate, ferric chloride, ferric ammonium sulfate, ferric lactate, ferric hydroxide, ferric citrate, etc. The iron or its compound is preferably used so that the platinum group metal:iron (atomic ratio) ratio is in the range of 10000:1 to 1:4, more preferably 5000:1 to 1:3. The catalyst containing iron or its compound can be prepared according to the well-known method.

Carbon monoxide to be used in Step (A) may be pure material, or may be diluted with an inert gas such as nitrogen, etc., or may contain a small amount of a hydrogen gas or methane. Further, in the present invention, carbon monoxide formed by decarbonylating the diaryl oxalate mentioned below may be used. The carbon monoxide formed by decarbonylating the diaryl oxalate is preferably reused in this step, after treating with an alkali, by feeding to an alkyl nitrite regenerating step to supplement the carbon monoxide consumed by the reaction or the carbon monoxide lost by purging of the circulating gas.

The reaction of Step (A) can be carried out, for example, by contacting a starting gas containing carbon monoxide and an alkyl nitrite in a vapor phase in the presence of s platinum group metal catalyst to prepare a dialkyl oxalate. At this time, the contacting time of the starting gas and the platinum group metal catalyst is preferably 10 seconds or shorter, more preferably 0.2 to 5 seconds, and the reaction temperature is preferably 50 to 200° C., more preferably 80 to 150° C. The reaction pressure is preferably normal pressure to 10 $kg/cm^2G$, more preferably normal pressure to 5 $kg/cm^2G$, and particularly preferably under pressure of 2 to 5 $kg/cm^2G$. As the reactor, a single pipe system, or a multi-pipe system heat-exchange type reactor is effective.

The concentration of the carbon monoxide in the starting gas is preferably in the range of 2 to 90% by volume. The concentration of the alkyl nitrite in the starting gas can be changed with a wide range, and for obtaining a satisfied reaction rate, the alkyl nitrite is to be present with a concentration of 1% by volume or more in the starting gas. The concentration of the alkyl nitrite in the starting gas is preferably in the range of, for example, 5 to 30% by volume.

In Step (A), a formed product (for example, a reaction gas) containing the dialkyl oxalate can be obtained. Then, the formed product (for example, a reaction gas) is led to a condenser to cool the temperature at which the dialkyl oxalate is condensed, so that they are separated to a condensed liquid containing the dialkyl oxalate and a non-condensed gas containing nitrogen monoxide. At this time, to prevent the dialkyl oxalate from accompanying to the non-condensed gas, 100 parts by weight of the product is preferably contacted with 0.001 to 0.1 part by volume of an alkyl alcohol at 30 to 60° C. The operating pressure of this step is preferably from normal pressure to 101 $g/cm^2G$, more preferably normal pressure to 5 $kg/cm^2G$, and particularly preferably under pressure of 2 to 5 $kg/cm^2G$.

Next, the dialkyl oxalate is separated from the condensed liquid and recovered. This operation is carried out, for example, by leading the condensed liquid to a distillation column and distillating the same by the usual manner since the condensed liquid contains a small amount of by-products such as a dialkyl carbonate, an alkyl formate, etc, in addition to the objective dialkyl oxalate. The separated and recovered dialkyl oxalate or/and an alkylaryl oxalate is/are fed to a step of transesterifing with an aryl alcohol.

On the other hand, the separated non-condensed gas contains nitrogen monoxide formed in Step (A) other than the unreacted carbon monoxide and the alkyl nitrite, and the nitrogen monoxide is led to the step of regenerating to an alkyl nitrite. Regeneration of the alkyl nitrite is carried out by leading the non-condensed gas to the bottom portion of a regeneration column and contacting with a molecular oxygen and an alkyl alcohol (reacting the nitrogen monoxide with a molecular oxygen and an alkyl alcohol). The gas (regenerating gas) led out from the regenerator is fed and circulated to Step (A) and reused. At this time, as the alkyl alcohol to be used, in addition to the newly fed alkyl alcohol from outside of the system, the following mentioned alkyl alcohol formed and recovered in the step of transesterification can be also used.

As the molecular oxygen, an oxygen gas or air, etc., can be used. As the regenerator, a usual gas-liquid contacting apparatus such as a packed column, a bubble column, a spray tower, a plate column, etc., can be used. In the regeneration of the alkyl nitrite, the reaction is so controlled that a concentration of the nitrogen monoxide in the regenerating gas is 2 to 7% by volume. Thus, the non-condensed gas is preferably contacted with the molecular oxygen and the alkyl alcohol at a temperature of the boiling point of the alkyl alcohol at the pressure of the regeneration or less (for example, from 0° C. to the boiling point of the alkyl alcohol) by feeding the molecular oxygen in an amount of 0.08 to 0.2 mol per mol of the nitrogen monoxide in the non-condensed gas to be led into the regenerator. The feeding amount of the alkyl alcohol is preferably 1 to 5 parts by volume based on 1 part by volume of the nitrogen monoxide in the non-condensed gas, and the contacting time is preferably 0.5 to 20 seconds. Also, the operating pressure is preferably from the normal pressure to 10 kg/cm$^2$G, more preferably from normal pressure to 5 kg/cm$^2$G, further particularly preferably 2 to 5 kg/cm$^2$G.

To the alkyl nitrite regenerating step is fed an alkali-treated (which has been subjected to washing with an aqueous alkaline solution and/or contact with an alkaline series adsorbent, etc.) carbon monoxide. The alkali-treated carbon monoxide is preferably led to the bottom portion of the regenerator. To the bottom portion of the regenerator, the non-condensed gas generated in Step (A) is, for example, fed by mixing with the non-condensed gas from the feeding line to be fed to the alkyl nitrite regenerating step, or may be fed separately and indepedndently. Be feeding the alkali-treated carbon monoxide to the alkyl nitrite regenerating step, lowering in selectivity of the dialkyl oxalate and lowering in catalyst activity in Step (A) can be effectively reduced.

When Step (A) is to be carried out in a continuous process, the carbon monoxide consumed by the reaction or the carbon monoxide lost from the system can by effectively supplemented by feeding carbon monoxide. Also, to supplement the nitrogen component lost from the system, an alkyl nitrite, nitrogen oxides (nitrogen monoxide, nitrogen dioxide, dinitrogen trioxide, dinitrogen tetroxide, etc.) or nitric acid is/are led to the bottom portion of the regenerator of the alkyl nitrite regenerating step. The carbon monoxide is thus supplemented (the nitrogen component is also supplemented depending on necessity), and a gas containing the regenerated alkyl nitrite (regenerating gas) is fed and circulated in Step (A).

[Aryl Alcohol]

The aryl alcohol to be used in the present invention may be mentioned, for example, phenol, o-cresol, m-cresol, p-cresol, 2-ethylphenol, 3-ethylphenol, 4-ethyl-phenol, 2,3-dimethylphenol, 2,4-dimethylphenol, 2,5-dimethylphenol, 3,4-dimethyl-phenol, etc. Among these, phenol is preferred in the viewpoint of reactivity and versatility.

[Diaryl Oxalate]

In the present invention, the diaryl oxalate to be prepared is not particularly limited, and may be mentioned, for example, diphenyl oxalate, bis(o-methylphenyl) oxalate, bis(p-methylphenyl) oxalate, bis(o-ethylphenyl) oxalate, bis(p-ethylphenyl) oxalate, etc.

[Catalyst (Trans Esterification Catalyst)]

In the preparation method of the diaryl oxalate of the present invention, a titanium compound is preferred as a catalyst for transesterification, and it is specifically mentioned TiX$_3$, Ti(OAc)$_3$, Ti(OBu)$_3$, Ti(OPh)$_3$, TiX$_4$, Ti(OAc)$_4$, Ti(OBu)$_4$, Ti(OPh)$_4$, etc. Here, Ac represents an acetyl group, Bu represents a butyl group, Ph represents a phenyl group, and X represents a halogen atom. Among these, Ti(OPh)$_4$ [tetraphenoxy titanium] having the same substituents as the starting material, i.e. the aryl alcohol, is particularly preferred since no impurity is by-produced.

Whereas the tetra(aryloxy)titanium can be difficultly obtained with an industrially used amount and is expensive, an aryl alcohol solution of the tetra(aryloxy)-titanium can be formed by reacting a tetraalkoxy titanium which is easily obtained with an industrial scale with an aryl alcohol. The tetraalkoxy titanium is not particularly limited, and there may be mentioned easily obtainable tetramethoxy titanium, tetraisopropoxy titanium, tetra-n-butoxy titanium, etc. Among these, tetraisopropoxy titanium is preferred in the points of easy in handling and commercial availability.

The aryl alcohol solution of the tetra(aryloxy)titanium can be prepared by heating a tetraalkoxy titanium such as tetraisopropoxy titanium, etc., and an aryl alcohol while removing a by-producing alkyl alcohol out of the system. The reaction of the tetraalkoxy titanium and an excess amount of the aryl alcohol is preferably carried out in a reaction-distillation column. The method of removing the by-producing alkyl alcohol out of the system is not particularly limited, and a method of removing the alkyl alcohol from the top of the column using a distillation column is preferred since the aryl alcohol or the tetraalkoxy titanium has a vapor pressure. In view of the continuous preparation, it is more preferred that the tetraalkoxy titanium and the aryl alcohol are fed for reaction and distillation, the aryl alcohol solution of the tetra(aryloxy) titanium is taken out from the bottom portion of the column, and the alkyl alcohol is removed from the top of the column out of the system while part of which is refluxing.

With regard to the portion of the starting materials to be fed into the distillation column, the tetraalkoxy titanium and the aryl alcohol as starting materials are preferably fed from the side portion of the distillation column to have a portion for the reaction and distillation, since if they are fed from the bottom portion of the distillation column, conversion of the tetraalkoxy titanium is sometimes lowered. As the system of the reaction-distillation column, a multiple stage distillation column using porous plate such as Oldershaw-type, a packed distillation column in which various kinds of fillers are packed, etc., can be utilized but the invention is not limited by these.

When the tetraalkoxy titanium and the aryl alcohol are to be reacted, the reaction sufficiently proceeds without any solvent particularly, and, if necessary, a solvent such as toluene, etc., which azeotropes with a by-producing alkyl alcohol may be added.

The aryl alcohol solution of the tetra(aryloxy)titanium is preferably fed to the step of transesterifying the dialkyl oxalate or/and the alkylaryl oxalate with the aryl alcohol continuously.

The aryl alcohol solution of the tetra(aryloxy)titanium may be prepared discontinuously, but preferably prepared continuously. When the aryl alcohol solution of the tetra(aryloxy) titanium is to be prepared continuously, the tetraalkoxy titanium and the aryl alcohol are fed to the reaction-distillation column continuously or discontinuously. The tetraalkoxy titanium and the aryl alcohol are preferably fed from the side portion of the reaction-distillation column.

The amount of the aryl alcohol to be added to the reaction-distillation column is preferably an excess amount to that of the tetraalkoxy titanium, and a molar ratio of the aryl alcohol and a titanium atom of the tetraalkoxy titanium (for example, tetraisopropoxy titanium) (molar number of the aryl alcohol/molar number of the titanium atom) is preferably 10 or more, more preferably 40 or more. The upper limit is preferably 80 or less, more preferably 60 or less. That is, a molar ratio of the aryl alcohol and the titanium atom of the tetraalkoxy titanium (molar number of the aryl alcohol/molar number of the titanium atom) is preferably 10 to 80, more preferably 40 to 80, further preferably 40 to 60, and particularly preferably 30 to 50. When the molar ratio is a little, the formed tetra(aryloxy) titanium is precipitated in the system to cause clogging, etc., in some cases, while the molar ratio is large, the apparatus tends to be unnecessarily large as compared with an amount of the forming tetra(aryloxy)-titanium.

A reflux ratio at the top portion of the column in the reaction distillation to carry out the reaction of the tetraalkoxy titanium and the aryl alcohol is preferably 3 to 40, and more preferably 5 to 20. If the reflux ratio is too low, there is a fear of lowering conversion rate. Also, if the reflux ratio is 40 or more, the progress rate of the reaction becomes slow.

It is preferred that the tetraalkoxy titanium and the excess amount of the aryl alcohol are continuously fed into the reaction-distillation column so that the molar ratio (aryl alcohol/titanium atom) of the titanium atom and the aryl alcohol in the reaction-distillation column is 40 to 80.

By feeding the tetraalkoxy titanium and the excess amount of the aryl alcohol to the reaction-distillation column to react them, removing fractions containing a by-producing alkyl alcohol, and taking out fractions containing the tetra(aryloxy) titanium and the aryl alcohol from the bottom portion, an aryl alcohol solution of the tetra(aryloxy)titanium from which the by-producing alkyl alcohol has been removed can be obtained. Then, the solution is preferably fed into the transesterification step.

The reaction temperature of the reaction of the tetraalkoxy titanium and the aryl alcohol is preferably maintained at 160 to 300° C., more preferably at 200 to 300° C. If the reaction temperature is low, conversion of the tetraisopropoxy titanium tends to be lowered. When tetraphenoxy titanium is used as the tetra(aryloxy)titanium, at a temperature of the melting point (153° C.) of the tetraphenoxy titanium or lower, there is a case where clogging occurs to cause difficulty in operation.

It is preferred that the tetra(aryloxy)titanium and the aryl alcohol are continuously taken out from the bottom portion of the reaction-distillation column, and the aryl alcohol solution of the tetra(aryloxy)titanium from which the by-producing alkyl alcohol has been removed is continuously fed to the transesterification step.

The aryl alcohol solution of the tetra(aryloxy)titanium obtained from the bottom portion of the reaction-distillation column is fed from the side portion of the reaction-distillation column as such without isolating and purifying the tetra(aryloxy)-titanium, with the dialkyl oxalate and the aryl alcohol, and used as a transesterification catalyst for preparing an alkylaryl oxalate or a diaryl oxalate. According to this, purification step of the catalyst can be markedly simplified and omitted, so that preparation facilities can be simplified and omitted, and a solvent for purification can be reduced whereby a load to environment can be reduced. Also, according to simplifycation of the steps, a detention time, thermal history against tetra(aryloxy)titanium, deterioration of water, etc., and contact with decomposed substances are reduced, and decomposed products can be controlled whereby selectivity of the diaryl oxalate and reaction efficiency can be improved.

[Material of the Apparatus]

In the preparation method of the diaryl oxalate of the present invention, a material of the apparatus (for example, inner wall of the distillation column, storage tank and pipings, structures in the distillation column such as a tray, packing materials, etc., more specifically a purification column of the diaryl oxalate, a reaction apparatus or reaction-distillation column for transesterification) which contact with the reaction solution of the transesterification is preferably an austenitic stainless steel containing 10% by weight or more of nickel and 1 to 4% by weight of molybdenum Further, the material of the apparatus is more preferably an austenitic stainless steel substantially not containing nitrogen atom.

Among the austenitic stainless steel, austenitic stainless steel containing 16.00 to 18.00% by weight of chromium is preferred, and austenitic stainless steel substantially not containing nitrogen atom is preferred. In the present invention, the austenitic stainless steel substantially not containing nitrogen atom means an austenitic stainless steel other than the high nitrogen stainless steel in which a nitrogen atom content is regulated in, for example, JIS G 4304, etc.

Further, among the austenitic stainless steel, SUS316 (Ni: 10.00 to 14.00% by weight, Cr: 16.00 to 18.00% by weight, Mo: 2.00 to 3.00% by weight, N: 0% by weight) or SUS316L (Ni: 12.00 to 15.00% by weight, Cr: 16.00 to 18.00% by weight, Mo: 2.00 to 3.00% by weight, N: 0% by weight) regulated by JIS G 4304 is more preferred.

When a carbon steel which has been well used as a usual material for an apparatus or a general austenitic stainless steel such as SUS304 (Ni: 8.00 to 10.50% by weight, Cr: 18.00 to 20.00% by weight, Mo: 0% by weight, N: 0% by weight) regulated by JIS G 4304, etc., is used at the portion contacting with a reaction mixture of the transesterification, material wastage or corrosion such as discloring of the surface, etc., is observed so that a continuous operation for a long period of time becomes difficult.

[Preparation Method of Diaryl Oxalate]

In the following, the method for preparing a diaryl oxalate in the presence of an aryl alcohol solution of the tetra(aryloxy)titanium as a catalyst is explained.

The process for preparing the diaryl oxalate comprises a step of transesterificating the dialkyl oxalate or/and alkylaryl oxalate with the aryl alcohol, and the obtained diaryl oxalate is separated and recovered.

A method for subjecting to transesterification may be mentioned, for example, the following methods.

First method is a process for preparing the diaryl oxalate by transesterifying the dialkyl oxalate or/and the alkylaryl oxalate with the aryl alcohol in the presence of the aryl alcohol solution of the tetra(aryloxy)titanium as a catalyst.

Second method is a process for preparing the diaryl oxalate by transesterifying the dialkyl oxalate or/and the alkylaryl oxalate with the aryl alcohol in the presence of the aryl alcohol solution of the tetra(aryloxy)titanium as a catalyst while removing the by-producing alkyl alcohol.

Third method is a process for preparing the diaryl oxalate by transesterifying the dialkyl oxalate or/and the alkylaryl oxalate with the aryl alcohol in the presence of the aryl alcohol solution of the tetra(aryloxy)titanium as a catalyst to form an alkylaryl oxalate, then, subjecting the alkylaryl oxalate to disproportionation reaction in the presence of the transesterification catalyst while removing the by-producing dialkyl oxalate.

Fourth method is a process for preparing the diaryl oxalate by transesterifying the dialkyl oxalate or/and the alkylaryl oxalate with the aryl alcohol in the presence of the aryl alcohol solution of the tetra(aryloxy)titanium as a catalyst while removing the by-producing alkyl alcohol by distillation to form an alkylaryl oxalate, then, subjecting the alkylaryl oxalate to disproportionation reaction in the presence of the transesterification catalyst while removing the dialkyl oxalate and the alkyl alcohol. Among these preparation methods, Fourth method is preferably used.

In the following, in the preparation method of the diaryl oxalate, it is explained by dividing into Step (B-1), Step (B-2) and Step (B-3).

In the alkylaryl oxalate-forming step (Step (B-1)) of the present invention, the alkylaryl oxalate can be formed, for example, by the following method.

[Step (B-1)]

The dialkyl oxalate formed in Step (A) is used for the alkylaryl oxalate-forming step (Step (B-1)). In Step (B-1), the dialkyl oxalate, the aryl alcohol and the aryl alcohol solution of the tetra(aryloxy)titanium as a catalyst is fed to First reaction-distillation column, and the dialkyl oxalate and the aryl alcohol are transesterified to form an alkylaryl oxalate while removing First vapor mainly comprising the alkyl alcohol from the top portion of First reaction-distillation column.

In First reaction-distillation column, a multi-step distillation column having a number of plates can be used. In First distillation column, in addition to the alkylaryl oxalate-forming step (Step (B-1)), disproportionation reaction (diaryl oxalate-forming reaction, Step (B-2)) is also partially carried out simultaneously.

In Step (B-1), it is preferred to feed the dialkyl oxalate, the aryl alcohol and the aryl alcohol solution of the tetra(aryloxy) titanium as a catalyst, each separately or in a mixed solution to the upper region of the number of the plates portion (or the portion of the packing materials) of First reaction-distillation column, and reacted. Also, it is preferred that the reaction mixture taken out from the bottom portion of First reaction-distillation column is fed to the upper region of the plates portion (or the portion of the packing materials) of Second reaction-distillation column, and reacted.

In First reaction-distillation column, First vapor mainly comprising the by-producing alkyl alcohol is preferably evaporated and taken out from the top portion of First reaction-distillation column. Also, a cooling apparatus is provided at the take out line connected to the top portion of First reaction-distillation column to condense First vapor, and it is removed as a condensed liquid mainly comprising an alkyl alcohol from the reaction system of the transesterification. In the condensed liquid mainly comprising the alkyl alcohol, an ether compound having a low boiling point is contained. The condensed liquid mainly comprising the alkyl alcohol is fed to Step (C) to reduce the concentration of the ether compound.

[Step (B-2)]

In the diaryl oxalate-forming step (Step (B-2)), the diaryl oxalate can be formed, for example, by the following method. Preferred is that the reaction mixture by transesterification is taken out from the bottom portion of First reaction-distillation column and fed it to Second reaction-distillation column, and while taking out Second vapor mainly comprising a dialkyl oxalate and further containing an alkyl alcohol from the top portion of Second reaction-distillation column, disproportionation reaction of an alkylaryl oxalate is carried out in the presence of the aryl alcohol solution of the tetra(aryloxy)titanium as a catalyst. Second vapor taken out from the top portio of Second reaction-distillation column is prefer-
ably reused by distillating the alkyl alcohol, if necessary, and feeding the fraction mainly comprising the dialkyl oxalate or the aryl alcohol to First reaction-distillation column.

First and Second reaction-distillation columns are preferably a reaction-distillation column comprising a distillation column having a number of plates, or a reaction-distillation column in which packing materials are filled at the upper portion, and which is a reaction-distillation column having a theoretical plate number of at least 2 steps or more, further preferably 5 to 100 steps, particularly preferably 7 to 50 steps. The multi-step distillation column type reaction-distillation column may be mentioned, for example, a plate system distillation column using bubble cap tray, porous plate tray, bubble tray, etc., or a packed systep distillation column in which various packing materials such as Raschig ring, Lessing ring, Pall ring, etc., are packed, and also, a reaction-distillation column having both of a plate system and packed system can be also used.

When the transesterification step is carried out in a liquid phase in which the reaction mixture is flow-down in First and Second reaction-distillation columns, the reaction temperature is preferably a temperature at which the reaction mixture containing starting materials and reaction products is melted or more, and a temperature at which the alkylaryl oxalate or the diaryl oxalate which are reaction products do not thermally decompose. The reaction temperature is preferably about 50 to 350° C., more preferably 100 to 300° C., and particularly preferably 120 to 280° C.

The reaction pressures in Step (B-1) and Step (B-2) may be either of a reduced pressure, normal pressure, or under pressure, and a temperature and a pressure which can evaporate the alkyl alcohol or the dialkyl oxalate which is a by-product are preferred. For example, when the reaction temperature is about 50 to 350° C., the reaction pressure is preferably 0.01 mmHg to 100 kg/cm$^2$G, more preferably 0.1 mmHg to 50 kg/cm$^2$G.

Also, the time of the reaction of the transesterification step (when a reaction-distillation column comprising a multi-step distillation column is used, detention time of the reaction mixture in First and Second reaction-distillation columns) may vary depending on the reaction conditions, the system of the reaction-distillation column and the operation conditions, and, for example, when the reaction temperature is about 50 to 350° C., it is preferably about 0.01 to 50 hours, more preferably 0.02 to 10 hours, and particularly preferably 0.05 to 5 hours.

Also, the ratio of the dialkyl oxalate and the aryl alcohol used in Step (B-1) and Step (B-2) may vary depending on the reaction conditions, etc., and, for example, the aryl alcohol is preferably 0.001 to 1000-fold mol based on the dialkyl oxalate to be fed, more preferably 0.1 to 100-fold mol, and particularly preferably 0.5 to 20-fold mol. Also, the amount of the aryl alcohol solution of the tetra(aryloxy)titanium to be used as a catalyst in the transesterification step may vary depending on the system and the size of the reaction apparatus, the kind of the starting materials and the composition, and further on the reaction conditions, and, for example, in terms of a ratio based on the total amount of the dialkyl oxalate and the aryl alcohol, it is preferably about 0.0001 to 50% by weight, more preferably 0.001 to 30% by weight, and particularly preferably 0.005 to 10% by weight.

[Step (B-3)]

The reaction mixture obtained in Step (B-1) and Step (B-2) mainly contains the starting materials and the aryl alcohol solution of the tetra(aryloxy)titanium as a catalyst, the alkylaryl oxalate as a reaction intermediate, and the diaryl oxalate as the objective material, the alkyl alcohol and the dialkyl oxalate, and an amount of the other by-products is extremely minute. Thus, for example, the objective diaryl oxalate can be easily separated and recovered from the reaction mixture obtained from Second reaction-distillation column by the usual distillation operation, etc.

As specific examples of the separation and recovery, there may be mentioned a method in which the reaction mixture obtained by the transesterification, etc., is distilled and/or evaporated by a distillation apparatus and/or evaporation apparatus to separate and recover the diaryl oxalate.

It is preferred that a titanium compound derived from the tetra(aryloxy)-titanium is removed from the reaction mixture containing the diaryl oxalate to make a concentration of the titanium compound in the reaction mixture containing the diaryl oxalate 10 ppm by weight or less. As the method for making the concentration of the titanium compound in the reaction mixture containing the diaryl oxalate 10 ppm by weight or less, there may be mentioned, for example, a method in which the reaction mixture obtained from Second reaction-distillation column is fed to a distillation apparatus or an evaporation apparatus, almost all the part of the reaction mixture is distilled or evaporated to remove the titanium compound. At this time, almost all the part of the reaction mixture evaporated is fed to the distillation column, and purified during the step of distilling and purifying the diaryl oxalate. The concentration of the titanium compound in the reaction mixture containing the diaryl oxalate is preferably 10 ppm by weight or less, more preferably 5 ppm by weight or less.

The reaction mixture containing the diaryl oxalate contains an aryl alcohol or an alkylaryl oxalate, etc., as impurities. However, the aryl alcohol or the alkylaryl oxalate has large difference in boiling point from that of the diaryl oxalate so that separation is easy, whereby even when distillation is carried out by using a distillation column with a relatively low plate number, a high purity diaryl oxalate can be obtained, for example, with purity of 97.0% by weight or more, and further 99.0% by weight or more.

When the obtained diaryl oxalate is used as a starting material of the diaryl carbonate, purity of the diaryl oxalate is sufficient with 97.0% by weight or more, and it is preferred that impurities (aryl alcohol, alkylaryl oxalate, etc.) are each 1.0% by weight or less, particularly 0.5% by weight or less, and further 0.1% by weight or less.

Also, as impurities, in addition to the aryl alcohol and the alkylaryl oxalate, a compound in which an oxalate having at least one aryl ester group or a decomposed product thereof has been subjected to Fries rearrangement and having a hydroxy group and an aryloxy group, or a compound in which the hydroxy group and the aryloxy group of the above compound has been intermolecularly or intramolecularly reacted is contained.

The method for distillating and purifying the aryl alcohol or the alkylaryl oxalate contained as impurites in the reaction mixture containing the diaryl oxalate may be mentioned, for example, a method of separating and recovering by fractionation as mentioned below.

The reaction mixture containing the diaryl oxalate is fed to First reaction-distillation column, and the vapor (vapor containing the alkylaryl oxalate and the aryl alcohol)as a low component is taken out from the top portion of First reaction-distillation column and condensed. Also, the column solution mainly comprising the diaryl oxalate is taken out from the bottom portion of First reaction-distillation column and fed to Second reaction-distillation column, and the vapor of the diaryl oxalate is taken out from the top portion of Second reaction-distillation column to recover the diaryl oxalate. The condensed liquid containing the alkylaryl oxalate and the aryl alcohol recovered from the top portion of First reaction-distillation column is preferably fed to the transesterification step (Step (B-1), etc.) to reuse the same.

It is possible to carry out separation and recovery of the diaryl oxalate by fractionation using First distillation column alone by simplifying and omitting the above-mentioned method. In this method, it is possible to carry out separation and recovery only by First reaction-distillation column by simplifying and omitting the method. For example, it can be carried out by the method in which the vapor component obtained by separating the titanium compound by an evaporator is fed to First reaction-distillation column, a low component vapor (alkylaryl oxalate and aryl alcohol) is taken out from the top portion thereof, and the diaryl oxalate is recovered by side cutting from the lower portion of the distillation column.

Further, the step of making the concentration of the titanium compound in the reaction mixture containing the diaryl oxalate 10 ppm by weight or less, and the step of removing the aryl alcohol and the alkylaryl oxalate contained in the reaction mixture as impurities can be carried out simultaneously.

There may be mentioned a method, for example, wherein the reaction mixture is firstly distilled in First reaction-distillation column, whereby a low component vapor (vapor containing alkylaryl oxalate and aryl alcohol) is removed from the top portion of First reaction-distillation column, and the column solution mainly comprising the diaryl oxalate is taken out from the bottom portion of First reaction-distillation column and fed to Second reaction-distillation column, then, a column solution containing the titanium compound is obtained from the bottom portion of Second reaction-distillation column, and a vapor of the diaryl oxalate is taken out from the top portion of Second reaction-distillation column and recovered.

It is also possible that the reaction mixture is fed to First reaction-distillation column, a low component vapor (vapor containing alkylaryl oxalate and aryl alcohol) is taken out from the top portion of First reaction-distillation column, and then, a vapor of the diaryl oxalate is taken out from the top portion, and the vapor of the diaryl oxalate is cooled and condensed to recover the same. Finally, a column solution containing the titanium compound can be removed from the bottom portion of First reaction-distillation column.

Among the above-mentioned methods that the aryl alcohol or the alkylaryl oxalate is distilled and purified from the reaction mixture to purify the diaryl oxalate, it is preferred to use the method in which the titanium compound, etc., are separated and the concentration of the titanium compound in the reaction mixture containing the diaryl oxalate is made 10 ppm by weight or less, then, the aryl alcohol and the alkylaryl oxalate are removed by distillation to purify the diaryl oxalate.

When purification of the reaction mixture containing the diaryl oxalate is carried out with the state at which the concentration of the titanium compound is high by distillation, etc., there is a case where furan compounds such as benzofuran-2,3-diones represented by the following formula (1) which are coloring substances are formed by heating one after another. The benzofuran-2,3-diones may be mentioned, for example, benzofuran-2,3-dione, etc.

Thus, formation of the furan compounds such as benzofuran-2,3-diones which are coloring components can be controlled by making the concentration of the titanium compound in the reation mixture 10 ppm by weight or less, and then, distillation and purification of the reaction mixture containing the diaryl oxalate are carried out.

[Formula 1]

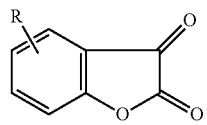

(1)

(wherein R represents a hydrocarbon group having 1 to 12 carbon atoms such as an alkyl group, an aralkyl group and an aryl group, a hydrogen atom or a halogen atom.)

Among the furan compounds, in particular, benzofuran-2,3-diones such as benzofuran-2,3-dione or an alkyl-substituted benzofuran-2,3-dione, etc., markedly affect coloring of the diaryl oxalate. Therefore, by making the benzofuran-2,3-dione concentration in the diaryl oxalate low, a less colored diaryl oxalate can be obtained.

Since the furan compound has a lower boiling point than that of the diaryl oxalate, when the vapor of the diaryl oxalate is taken out from the top portion of the distillation column, the furan compound formed in the column solution is accompanied by the vapor of the diaryl oxalate. Also, even when the vapor of the furan compound is intended to be taken out from the top portion of the distillation column, the furan compound is newly formed by heating the column solution so that it is difficult to make the concentration of the furan compound in the diaryl oxalate low.

In the distillation operation, it cannot be carried out in the high purity state without coloring, so that it is important to make the concentration of the titanium compound as low as possible during distillation and purification. When the titanium compound is substantially not contained, a formation rate of the furan compound such as benzofuran-2,3-dione is slow, so that the diaryl oxalate and the furan compound can be easily separated by distillation.

The diaryl oxalate obtained by the preparation method of the present invention is subjected to the above-mentioned purification step, etc., if necessary, and the concentration of the furan compound contained in the diaryl oxalate is preferably 500 ppm or less.

The furan compound causes coloring of the diaryl oxalate. Therefore, if the concentration of the furan compound contained in the diaryl oxalate is 500 ppm or less, the diaryl oxalate having high transparency can be obtained.

The concentration of the furan compound contained in the diaryl oxalate is preferably 400 ppm or less, more preferably 300 ppm or less.

The furan compound may be mentioned benzofuran-2,3-diones such as benzofuran-2,3-dione, etc. In particular, benzofuran-2,3-dione is a great cause of coloring of the diaryl oxalate. Therefore, the concentration of the benzofuran-2,3-dione in the diaryl oxalate is preferably made 500 ppm or less, more preferably 400 ppm or less, and further preferably 300 ppm or less.

Also, the diaryl oxalate obtainable by the preparation process of the present invention preferably has a melt Hazen color index at 150° C. in an atmosphere of No. 200 or less.

The diaryl oxalate is frequently used as a starting material of a diaryl carbonate. When a colored diaryl oxalate is used as a starting material, it causes a colored diaryl carbonate, and preparation of a high purity diaryl carbonate is inhibited. Also, in the diaryl carbonate-forming step, the furan compound, etc., in the diaryl oxalate causes formation of a high-boiling point compound. Thus, the presence of a large amount of the furan compound in the diaryl oxalate causes lowering in selectivity or yield of the diaryl carbonate in the diaryl carbonate-forming step.

[Step (C)]

In the present invention, when the dialkyl oxalate and the aryl alcohol are transesterified in Step (B-1), a by-producing alkyl alcohol is recovered and recycled into the dialkyl oxalate-forming step (Step (A)). In the alkyl alcohol, impurities such as a low-boiling point ether compound, etc., are migrated, and among various kinds of imprities, the ether compound itself shall be definitely required to reduce its concentration. This is because, if the alkyl alcohol containing the ether compound with a certain concentration or more is used in the dialkyl oxalate-forming step (Step (A)), yield or selectivity of the dialkyl oxalate is markedly lowered. Also, in Step (B-2), with regard to the alkyl alcohol taken out depending on necessity from Second vapor which is taken out from the top portion of Second reaction-distillation column, it is preferred to reduce the concentration of the low-boiling point ether compound similarly.

The ether compound may be mentioned, for example, an alkyl aryl ether such as anisole and dimethyl ether, or diphenyl ether. The content of the ether compound in the alkyl alcohol is required to be less than 1000 ppm by weight, and of these, preferably 500 ppm by weight or less, more preferably 300 ppm by weight or less, particularly preferably 100 ppm by weight or less. In particular, if the content of the alkyl aryl ether such as anisole in the alkyl alcohol is larger, yield of the dimethyl oxalate in Step (A) is low, so that it is preferred to reduce the content of the alkyl aryl ether such as anisole in the alkyl alcohol.

A method for reducing the concentration of the ether compound in the alkyl alcohol may be mentioned, for example, the following methods.

The vapor mainly containing the alkyl alcohol taken out from the top portion of First reaction-distillation column in Step (B-1), or/and the vapor containing the alkyl alcohol taken out depending on necessity from Second vapor which is taken out from the top portion of Second reaction-distillation column in Step (B-2) is/are cooled and condensed, and the alkyl alcohol containing the ether compound with a relatively high concentration can be obtained. The alkyl alcohol containing the ether compound with a relatively high concentration is distilled to separate the alkyl alcohol, whereby the concentration of the ether compound can be reduced.

[Preparation Step of Diaryl Carbonate]

The obtained diaryl oxalate is decarbonylated to from a diaryl carbonate and carbon monoxide, and the diaryl carbonate can be separated and recovered from the reaction mixture. This decarbonylation is preferably carried out in a liquid phase in the presence of a catalyst.

When the decarbonylation of the diaryl oxalate is carried out in a liquid phase, the catalyst preferably used is a catalyst which can carry out the decarbonylation of the diaryl oxalate at relatively low temperature (about 100 to 350° C.), and give the diaryl carbonate with high selectivity (at least 50% or more, in particular 60 to 100%).

The catalyst used in the liquid phase may be mentioned a catalyst comprising, for example, an organic phosphorus compound, preferably an organic phosphorus compound having at least one carbon-phosphorus bond. Such an organic phosphorus compound may be mentioned at least one organic phosphorus compound selected from a phosphine (w), a phosphine oxide (x), a phosphine dihalide (y) and a phosphonium salt (z) represented by the formulae (w) to (z).

[Formula 2]

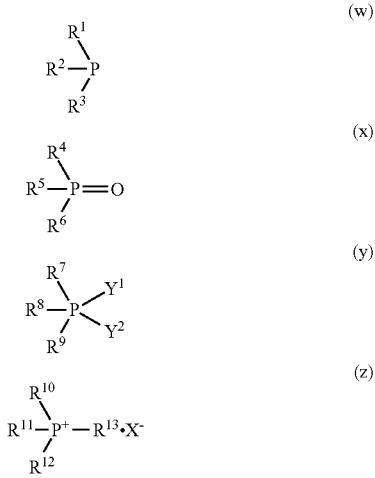

(wherein $R^1$ to $R^{13}$ each represent at least one group selected from an alkyl group having 1 to 16 carbon atoms, an aryl group having 6 to 16 carbon atoms and an aralkyl group having 7 to 22 carbon atoms, X represents an atom or an atomic group capable of forming a counter ion, and $Y^1$ and $Y^2$ each represent a halogen atom such as a chlorine atom, a bromine atom, an iodine atom, etc. At least one of compounds (w) to (z) has the above-mentioned group(s).)

The group(s) shown by $R^1$ to $R^{13}$ may be mentioned, for example, an alkyl group having 1 to 16 carbon atoms (methyl group, ethyl group, n-propyl group, i-propyl group, n-butyl group, i-butyl group, n-pentyl group, etc.), an aryl group having 6 to 16 carbon atoms (phenyl group, methylphenyl group, ethylphenyl group, methoxyphenyl group, ethoxyphenyl group, chlorophenyl group, fluorophenyl group, naphthyl group, methylnaphthyl group, methoxynaphthyl group, chloronaphthyl group, etc.), and an aralkyl group having 7 to 22 carbon atoms (benzyl group, phenethyl group, 4-methyl-benzyl group, 4-methoxybenzyl group, p-methylphenethyl group, etc.). The aryl group and the aralkyl group may have at least one substituent(s) selected from an alkyl group having 1 to 16 carbon atoms, an alkoxy group having 1 to 16 carbon atoms, a nitro group and a halogen atom (a fluorine atom, a chlorine atom, a bromine atom, etc.) as a substituent(s) directly bonding to the carbon atom forming the aromatic ring.

The organic phosphorus compounds (w) to (z) may be preferably those wherein all of the groups ($R^1$ to $R^{13}$) are aryl groups, but it may be a compound wherein 1 to 2 (in particular, 2) of the substituent is/are an aryl group(s), and the remainder is/are an alkyl group(s) or an aralkyl group(s). The phosphine wherein all of $R^1$ to $R^3$ of the formula (w) are aryl groups may be mentioned, for example, triphenylphosphine, tris(4-chlorophenyl)phosphine and tris(4-tolyl)phosphine. The phosphine oxide wherein all of $R^4$ to $R^6$ of the formula (x) are aryl groups may be mentioned, for example, triphenylphosphine oxide, tris(4-chlorophenyl)phosphine oxide and tris(4-tolyl)phosphine oxide. The phosphine dihalide wherein all of $R^7$ to $R^9$ of the formula (y) are aryl groups may be mentioned, for example, triphenylphosphine dichloride and triphenylphosphine dibromide. Among the phosphine dihalides, a triarylphosphine dichloride such as triphenylphosphine dichloride, etc., is preferred.

As the phosphonium salt of the formula (z), a phosphonium salt wherein all of $R^{10}$ to $R^{13}$ are aryl groups, and the counter ion $X^-$ is a halogen ion, an aliphatic carboxylic acid ion or a fluoroborate ion, etc., is preferred, and it may be a compound wherein 1 to 3 of $R^{10}$ to $R^{13}$, particularly 2 or 3 of the same is/are an aryl group(s), and the remainder is/are an aralkyl group(s) or alkyl group(s), and further the counter ion $X^-$ is a halogen ion, an aliphatic carboxylic acid ion or a fluoroborate ion. The phosphonium salt wherein all of $R^{10}$ to $R^{13}$ of the formula (z) are aryl groups may be mentioned, for example, a phosphonium salt wherein the counter ion $X^-$ is a halogen ion such as tetraphenylphosphonium chloride, tetraphenylphosphonium bromide, 4-chlorophenyl-triphenylphosphonium chloride, 4-chlorophenyltriphenylphosphonium bromide, 4-ethoxyphenyltriphenylphosphonium chloride, 4-ethoxyphenyltriphenylphosphonium bromide, 4-methylphenyltriphenylphosphonium chloride, 4-methylphenyltriphenyl-phosphonium bromide, etc.

Among the organic phosphorus compounds, the tetraarylphosphonium salt is preferred. Of these, a tetraarylphosphonium halide is more preferred, and a tetraarylphosphonium chloride such as tetraphenylphosphonium chloride, etc., is particularly preferred. The decarbonylation catalyst comprising the organic phosphorus compound may be used singly or a mixture of two or more compounds, and may be uniformly dissolved and/or suspended in the reaction mixture. An amount of the organic phosphorus compound to be used in the decarbonylation step is preferably 0.001 to 50 mol %, more preferably 0.01 to 20 mol % or so based on the amount of the diaryl oxalate.

To the decarbonylation catalyst comprising the organic phosphorus compound may be preferably added at least one inorganic or organic halogen-substituted compound series additive depending on necessity. When a phosphine or a phosphine oxide is used as the organic phosphorus compound, or a phosphonium salt other than a halide and a hydrogen dihalide is used, the halogen compound series additive is preferably added. An amount of the halogen compound series additive to be added is preferably 0.01 to 150-fold mol, more preferably 0.05 to 100-fold mol based on the amount of the organic phosphorus compound.

The inorganic halogen compound series additive may be mentioned, for example, a halogenated material of aluminum (aluminum chloride, aluminum bromide, etc.), a halogenated material of a platinum group metal (platinum chloride, ruthenium chloride, palladium chloride, etc.), a halogenated material of phosphorus (phosphorus pentachloride, etc.), a halogenated material of sulfur (thionyl chloride, etc.), a halogenated hydrogen (hydrogen chloride, etc.), a halogen (chlorine, etc.). Also, the organic halogen compound series additive may be mentioned, for example, a material having a structure in which a halogen atom is bonded to a saturated carbon (C—Hal), or a structure in which a halogen atom is bonded to a carbonyl carbon (CO—Hal). Such an organic halogen compound series additive may be mentioned, for example, a halogenated alkyl (alkyl chlorides such as chloroform, carbon tetrachloride, 1,2-dichloroethane, butyl chloride, etc.), a halogenated aralkyl (an aralkyl chloride such as benzyl chloride, etc.), halogen-substituted aliphatic carboxylic acid (chloroacetic acid, bromoacetic acid, etc.), an acid halide (an acid chloride such as oxalyl chloride, propionyl chloride and benzoyl chloride, etc.). Here, Hal represents a halogen atom such as a chlorine atom, a bromine atom, etc.

Decarbonylation of the diaryl oxalate is preferably carried out by feeding a diaryl oxalate to a reactor in which a catalyst mainly comprising an organic phosphorus compound (and a halogen compound series additive depending on necessity) is present, and decarbonylating the diaryl oxalate in a liquid phase to form a diaryl carbonate, while removing generating carbon monoxide. At this time, the reaction temperature is preferably 100 to 450° C., more preferably 160 to 400° C., particularly preferably 180 to 350° C. The reaction pressure is not particularly limited, and may be in the range of, for example, 10 mmHg to 10 kg/cm$^2$G. When the fact that carbon monoxide formed in the decarbonylation step is treated with an alkali and supplied to a regeneration step of methyl nitrite is considered, it is preferably from a normal pressure to 10 kg/cm$^2$G, more preferably from a normal pressure to 5 kg/cm$^2$G, particularly preferably in the range of 2 to 5 kg/cm$^2$G. Any specific solvent is required for the reaction, but an aprotic solvent such as diphenyl ether, sulfolane, N-methylpyrrolidone, dimethyl-imidazolidone, etc., may be used, if necessary.

As the reactor for decarbonylation, any type of the reactor can be used so long as it can form a diaryl carbonate with carbon monoxide by decarbonylating a diaryl oxalate in the presence of an organic phosphorus compound. For example, when the decarbonylation of the diaryl oxalate is carried out in a liquid phase, there may be used a single tank or a multi-tank completely mixing type reactor (a stirring tank), a tower type reactor, etc. The material of the reactor is not particularly limited so long as it has a sufficient heat resistance in decarbonylation of a diaryl oxalate, for example, there may be conveniently used a glass, stainless steel (SUS), aluminum alloy, nickel alloy, etc.

In the reaction mixture obtained by decarbonylation of the diaryl oxalate, unreacted diaryl oxalate or an organic phosphorus compound is contained. Thus, it is suitably used the method to separate and recover the diaryl carbonate from the reaction mixture that, the catalyst is separated by an evaporation apparatus such as a falling film evaporator, a thin film evaporator, etc., to recover the same, and then, the evaporated component is distilled by using a distillation apparatus such as a packed column having a certain degree of a theoretical plate number (in particular, 5 to 50 steps) or a plate column, etc. Also, it may be used the method that the reaction mixture is distilled by a distillation apparatus such as a packed column or a plate column, etc., so that the diaryl carbonate is taken out from the top portion of the column, and the column solution containing the unreacted diaryl oxalate or an organic phosphorus compound is taken out from the bottom portion of the column. The taken out column solution is fed to the reactor for decarbonylation for circulation. According to the above method, the diaryl carbonate is separated and recovered from the reaction mixture to obtain a high purity diaryl carbonate.

[Preparation Method of Polycarbonate]

The prepared diaryl carbonate is reacted with bisphenol A in the presence of a basic alkali metal salt to obtain a polycarbonate.

Examples of the basic alkali metal salt may be mentioned, for example, sodium hydroxide, potassium hydroxide, lithium hydroxide, cesium hydroxide, sodium hydrogen carbonate, potassium hydrogen carbonate, lithium hydrogen carbonate, cesium hydrogen carbonate, sodium carbonate, potassium carbonate, lithium carbonate, cesium carbonate, sodium acetate, potassium acetate, lithium acetate, cesium acetate, sodium stearate, potassium stearate, lithium stearate, cesium stearate, sodium borohydride, potassium borohydride, lithium borohydride, cesium borohydride, sodium phenyl borate, potassium phenyl borate, lithium phenyl borate, cesium phenyl borate, sodium benzoate, potassium benzoate, lithium benzoate, cesium benzoate, disodium hydrogen phosphate, dipotassium hydrogen phosphate, dilithium hydrogen phosphate, dicesium hydrogen phosphate, disodium phenylphosphate, dipotassium phenylphosphate, dilithium phenylphosphate, dicesium phenylphosphate, alcoholate or phenolate of sodium, potassium, lithium or cesium, disodium salt, dipotassium salt, dilithium salt or dicesium salt of bisphenol A, etc.

An amount of the basic alkali metal salt is not particularly limited, and can be used, for example, in the range of $1 \times 10^{-9}$ to $1 \times 10^{-3}$ mol per mole of bisphenol A. In an alkali metal compound which is particularly good in view of physical property and handling, an amount of the basic alkali metal salt is preferably in the range of $1 \times 10^{-8}$ to $1 \times 10^{-5}$ mol, particularly preferably $2 \times 10^{-8}$ to $8 \times 10^{-6}$ mol per mole of bisphenol A. If an amount of the basic alkali metal salt to be added is too little, there is a tendency that required polymerization activity cannot be obtained, while if the amount added is too much, the color hue of the polymer is worsened, and a branched chain tends to be increased.

In combination with the basic alkali metal salt, it is possible to use a basic compound such as a basic boron compound, a basic phosphorus compound, a basic ammonium compound or an amine type compound, etc., as an auxiliary catalyst.

Specific examples of the basic boron compound may be mentioned such as tetramethyl boron, tetraethyl boron, tetrapropyl boron, tetrabutyl boron, trimethylethyl boron, trimethylbenzyl boron, trimethylphenyl boron, triethylmethyl boron, triethylbenzyl boron, triethylphenyl boron, tributyl benzyl boron, tributyl phenyl boron, tetraphenyl boron, benzyltriphenyl boron, methyltriphenyl boron, butyl triphenyl boron, etc.

The basic phosphorus compound may be mentioned, for example, triethyl-phosphine, tri-n-propylphosphine, triisopropylphosphine, tri-n-butylphosphine, triphenylphosphine, tributylphosphine, or a quaternary phosphonium salt, etc.

The basic ammonium compound may be mentioned, for example, tetramethyl ammonium hydroxide, tetraethyl ammonium hydroxide, tetrapropyl ammonium hydroxide, tetrabutyl ammonium hydroxide, trimethylethyl ammonium hydroxide, trimethylbenzyl ammonium hydroxide, trimethylphenyl ammonium hydroxide, triethylmethyl ammonium hydroxide, triethylbenzyl ammonium hydroxide, triethylphenyl ammonium hydroxide, tributyl benzyl ammonium hydroxide, tributyl phenyl ammonium hydroxide, tetraphenyl ammonium hydroxide, benzyltriphenyl ammonium hydroxide, methyltriphenyl ammonium hydroxide, butyl triphenyl ammonium hydroxide, etc.

The amine type compound may be mentioned, for example, 4-aminopyridine, 2-aminopyridine, N,N-dimethyl-4-aminopyridine, 4-diethylaminopyridine, 2-hydroxy-pyridine, 2-methoxypyridine, 4-methoxypyridine, 2-dimethylaminoimidazole, 2-methoxyimidazole, imidazole, 2-mercaptoimidazole, 2-methylimidazole, amino-quinoline, etc.

The method for preparing a polycarbonate by reacting the prepared diaryl carbonate with bisphenol A in the presence of a basic alkali metal salt, there may be mentioned, for example, the following method. By mixing 1.07 of the diphenyl carbonate in a molar ratio with 1 of bisphenol A, the mixture is maintained at 130° C., and 1 ml of 0.01N sodium hydroxide (1 µmol based on 1 mol of bisphenol A) was charged to the mixed melted material under nitrogen atmosphere. Then, polycondensation reaction is carried out at 210° C./100 mmHg for 60 minutes, 240° C./15 mmHg for 60 minutes, and 280° C./0 5 mmHg for 2 hours, while removing the by-producing phenol at an optional time by distillation to obtain an aromatic polycarbonate having a viscosity average molecular weight of 20,000, and the material is cut with a cutter to make pellets.

EXAMPLES

In the following, the present invention is described in detail by referring to Examples. However, the present invention is not limited by the following Examples.

Synthetic Example 1

Synthesis of Tetraphenoxy Titanium

To the bottom of an Oldershaw type reaction-distillation column (hereinafter referred to as "reaction-distillation column for synthesizing a catalyst") having an inner diameter of 32 mm and equipped with a bottom flask having a volume of 1L was charged 300 ml of phenol, and heated by an oil bath. While maintaining the whole refluxing state, and after stabilization of the temperature distribution in the reaction-distillation column for synthesizing a catalyst, phenol was fed with a flow amount of 342.4 g/h, and tetraisopropoxy titanium (TIPT) with 21.6 g/h. The ratio of the molar number of the phenol fed and the molar number of of the Ti atom in TIPT (phenol/Ti) was 48. The distilled liquid from the top was taken out while maintaining the reflux ratio of 5. With regard to the bottom, the liquid was continuously taken out from the bottom portion of the reaction-distillation column for synthesizing a catalyst so that the liquid surface maintained 330 ml. With this state, it was maintained until the system became a steady state, and when the bottom liquid was analyzed, 10.8% by weight of tetraphenoxy titanium (TPT), 89.2% by weight of phenol and 114 ppm of isopropanol (IPA) were detected. Also, the composition of the distillate was 71.8% by weight of phenol and 28.2% by weight of isopropanol. The taken out amounts at that time were the bottom liquid of 295.4 g/h and the top distillate of 68.6 g/h. Also, the bottom temperature was 190° C., and the top temperature was 164° C. As a result, the conversion of TIPT to TPT (TPT yield) was 99.8%. The reaction conditions and the results are shown in Table 1.

TIPT conversion was obtained by the following formula.

[Numerical Formula 1]

[(Bottom TPT amount (wt %)×284.3/419.9)−(Bottom IPA amount (ppm)/10,000×284.3/(60.1×4))]/ (Bottom TPT amount (wt %)×284.3/419.9)×100 (%)

Synthetic Examples 2 to 4

Synthesis of Tetraphenoxy Titanium

The same experiment as in Synthetic example 1 was carried out by changing a part of the conditions as shown in Table 1 and the results are also shown in Table 1.

In the reaction mixture of Synthetic example 4, TPT was partially precipitated.

Synthetic Example 5

Synthesis of tetraphenoxy titanium was carried out in the same manner as in Synthetic example 1 except for feeding tetraisopropoxy titanium to the bottom. As a result, the conversion of TIPT to TPT (TPT yield) was 93.1%.

TABLE 1

| Synthetic example | Reflux ratio | Pressure (Bottom temperature) | PhOH/TIPT feed molar ratio | TPT yield (%) |
|---|---|---|---|---|
| 1 | 5 | 760 mmHg (190° C.) | 48 | 99.8 |
| 2 | 20 | 760 mmHg (190° C.) | 48 | 99.8 |
| 3 | 20 | 380 mmHg (159° C.) | 48 | 99.5 |
| 4 | 20 | 760 mmHg (190° C.) | 30 | 99.7 |
| 5 | 5 | 760 mmHg (190° C.) | 48 | 93.1 |

Example 1

To the bottom of Oldershaw type reaction-distillation column (distillation column inner diameter: 32 mm, total step number: 50 steps, in the following, referred to as "First reaction-distillation column") and equipped with a bottom flask having a volume of 1 L was charged 300 ml of a mixed liquid (PhOH/DMO molar ratio of 2/1) of phenol (PhOH) and dimethyl oxalate (DMO), and the mixture was heated by an oil bath to reactive distillate the mixture. When the mixture became stable with whole reflux, from the top of the column, a mixed liquid comprising 61.4% by weight of phenol and 38.6% by weight of dimethyl oxalate was fed with 300 ml/h, and the bottom liquid (phenol solution of TPT) taken out from the bottom portion of the reaction-distillation column for synthesizing a catalyst of Synthetic example 1 was fed with 9 ml/h. When methanol was starting to distill out from the top, the reflux ratio was made 2 and a taken out operation was started. The bottom liquid was also started to be taken out continuously so that the liquid surface maintained at 300 ml.

At the time (5 hours after starting feeding) at which the state of the column became stable, when the composition of the bottom liquid was analyzed by gas chromatography, it was 6.75% by weight of diphenyl oxalate, 26.77% by weight of methylphenyl oxalate, 23.23% by weight of dimethyl oxalate and 42.91% by weight of phenol. Also, the distillate from the top had the composition comprising 99.7% by weight of methanol and 0.3% by weight of dimethyl oxalate.

Example 2

To the bottom flask of First reaction-distillation column was charged 300 ml of a mixed liquid (PhOH/DMO molar ratio of 2/1) of phenol (PhOH) and dimethyl oxalate (DMO), and the mixture was heated by an oil bath to react the mixture. When the mixture became stable with whole reflux, a mixed liquid comprising 61.4% by weight of phenol and 38.6% by weight of dimethyl oxalate was fed from the top of the column with 300 ml/h, and the bottom liquid (phenol solution of TPT) taken out from the bottom portion of the reaction-distillation column for synthesizing a catalyst of Synthetic example 2 was fed with 9 ml/h. When methanol was starting to distill out from the top, the reflux ratio was made 2 and a taken out operation was started. The bottom liquid was also started to be taken out continuously so that the liquid surface maintained at 300 ml.

At the time (5 hours after starting feeding) at which the state of the column became stable, when the composition of the bottom liquid was analyzed by gas chromatography, it was 6.72% by weight of diphenyl oxalate, 26.80% by weight of methylphenyl oxalate, 23.20% by weight of dimethyl oxalate and 42.94% by weight of phenol. Also, the distillate from the top had the composition comprising 99.7% by weight of methanol and 0.3% by weight of dimethyl oxalate.

Example 3

To the bottom flask of First reaction-distillation column was charged 300 ml of a mixed liquid (PhOH/DMO molar ratio of 2/1) of phenol (PhOH) and dimethyl oxalate (DMO), and the mixture was heated by an oil bath to react the mixture. When the mixture became stable with whole reflux, a mixed liquid comprising 61.4% by weight of phenol and 38.6% by weight of dimethyl oxalate was fed from the top of the column with 300 ml/h, and the bottom liquid (phenol solution of TPT) taken out from the bottom portion of the reaction-distillation column for synthesizing a catalyst of Synthetic example 3 was fed with 9 ml/h. When methanol was starting to distill out from the top, the reflux ratio was made 2 and a taken out operation was started. The bottom liquid was also started to be taken out continuously so that the liquid surface maintained at 300 ml.

At the time (5 hours after starting feeding) at which the state of the column became stable, when the composition of the bottom liquid was analyzed by gas chromatography, it was 6.68% by weight of diphenyl oxalate, 26.82% by weight of methylphenyl oxalate, 23.25% by weight of dimethyl oxalate and 42.91% by weight of phenol. Also, the distillate from the top had the composition comprising 99.7% by weight of methanol and 0.3% by weight of dimethyl oxalate.

Example 4

To the bottom flask of First reaction-distillation column was charged 300 ml of a mixed liquid (PhOH/DMO molar ratio of 2/1) of phenol (PhOH) and dimethyl oxalate (DMO), and the mixture was heated by an oil bath to react the mixture. When the mixture became stable with whole reflux, a mixed liquid comprising 61.4% by weight of phenol and 38.6% by weight of dimethyl oxalate was fed from the top of the column with 300 ml/h, and the bottom liquid (phenol solution of TPT) taken out from the bottom portion of the reaction-distillation column for synthesizing a catalyst of Synthetic example 4 was fed with 9 ml/h. When methanol was starting to distill out from the top, the reflux ratio was made 2 and a taken out operation was started. The bottom liquid was also started to be taken out continuously so that the liquid surface maintained at 300 ml.

At the time (5 hours after starting feeding) at which the state of the column became stable, when the composition of the bottom liquid was analyzed by gas chromatography, it was 6.70% by weight of diphenyl oxalate, 26.84% by weight of methylphenyl oxalate, 23.25% by weight of dimethyl oxalate and 42.91% by weight of phenol. Also, the distillate from the top had the composition comprising 99.7% by weight of methanol and 0.3% by weight of dimethyl oxalate.

Example 5

To the bottom flask of First reaction-distillation column was charged 300 ml of a mixed liquid (PhOH/DMO molar ratio of 2/1) of phenol (PhOH) and dimethyl oxalate (DMO), and the mixture was heated by an oil bath to react the mixture. When the mixture became stable with whole reflux, a mixed liquid comprising 61.4% by weight of phenol and 38.6% by weight of dimethyl oxalate was fed from the top of the column with 300 ml/h , and the bottom liquid (phenol solution of TPT) taken out from the bottom portion of the reaction-distillation column for synthesizing a catalyst of Synthetic example 5 was fed with 9 ml/h. When methanol was starting to distill out from the top, the reflux ratio was made 2 and a taken out operation was started. The bottom liquid was also started to be taken out continuously so that the liquid surface maintained at 300 ml.

At the time (5 hours after starting feeding) at which the state of the column became stable, when the composition of the bottom liquid was analyzed by gas chromatography, it was 5.40% by weight of diphenyl oxalate, 27.34% by weight of methylphenyl oxalate, 24.01% by weight of dimethyl oxalate and 42.95% by weight of phenol. Also, the distillate from the top had the composition comprising 99.7% by weight of methanol and 0.3% by weight of dimethyl oxalate.

Comparative Example 1

In the same manner as in Example 1 except for feeding 7.6% by weight TIPT phenol solution with 8.5 ml/h in place of the phenol solution of TPT obtained in Synthetic example 1, transesterification of phenol and dimethyl oxalate was carried out continuously.

At the time (5 hours after starting feeding) at which the state of the column became stable, when the composition of the bottom liquid was analyzed by gas chromatography, it was 6.63% by weight of diphenyl oxalate, 26.33% by weight of methylphenyl oxalate, 23.48% by weight of dimethyl oxalate, 43.38% by weight of phenol, and peaks of isopropyl phenyl oxalate and methylisopropyl oxalate with minute amount were detected. Also, the distillate (about 25 ml/h) from the top had the composition comprising 98.4% by weight of methanol, 1.4% by weight of isopropanol and 0.2% by weight of dimethyl oxalate.

Example 6

From the upper portion of Oldershaw of First reaction-distillation column, a mixed liquid comprising 61.4% by weight of phenol and 38.6% by weight of dimethyl oxalate was fed with 330 g/h, and the bottom liquid (phenol solution of TPT) taken out from the bottom portion of the reaction-distillation column for synthesizing a catalyst of Synthetic example 1 was fed with 9 ml/h. The bottom flask was heated to 190° C., and transesterification was carried out while the vapor from the top portion of the column was condensed with the condenser and taken out with the reflux ratio of 2.

At the time (5 hours after starting feeding) at which the state of the column became stable, when the composition of the bottom liquid was analyzed by gas chromatography, it was 6.74% by weight of diphenyl oxalate, 26.76% by weight of methylphenyl oxalate, 23.45% by weight of dimethyl oxalate and 42.62% by weight of phenol. An amount of the bottom liquid taken out from the column was about 306 g/h. From the top of the column, the liquid with the composition comprising 99.7% by weight of methanol and 0.3% by weight of dimethyl oxalate was taken out with about 24 g/h.

As Second reaction-distillation column, the same type of Oldershaw type reaction-distillation column as First reaction-distillation column was used, and to the $12^{th}$ step from the top of Second reaction-distillation column was fed the reaction mixture after the above-mentioned transesterification with 300 ml/h. The bottom flask was heated by a mantle heater to 230° C., and disproportionation reaction was carried out while condensing the vapor from the top portion of the column by the condenser without reflux, and taking out of the system. At the time (5 hours after starting feeding) at which the state of the column became stable, when the composition of the bottom liquid was analyzed by gas chromatography, it was 53.22% by weight of diphenyl oxalate, 25.81% by weight of methylphenyl oxalate, 2.37% by weight of dimethyl oxalate and 17.14% by weight of phenol. An amount of the bottom liquid taken out from the column was about 132 g/h. From the top portion of the column, the liquid having the composition comprising 2.32% by weight of methanol, 43.75% by weight of dimethyl oxalate, 50.16% by weight of phenol, 3.64% by weight of methylphenyl oxalate and 0.13% by weight of diphenyl oxalate was taken out with about 189 g/h.

To the rotary thin film evaporator (heat transfer area: 0.1 m$^2$) the pressure of which had been reduced to 20 mmHg was fed the bottom liquid of the column (the reaction mixture) obtained above with 100 ml/h, and the evaporator was heated to 200° C. by a heating medium, dimethyl oxalate, phenol, methylphenyl oxalate and dimethyl oxalate were continuously evaporated and condensed by the condenser. From the bottom portion of the evaporator, the liquid containing about 20% by weight of tetraphenoxy titanium was taken out with about 7 g/h.

Incidentally, the piping from the vapor outlet of the thin film evaporator to the condenser was made a raising piping, and a demister was used by providing at the raising piping portion of the evaporator and the condenser.

By using a distillation column made of a glass packed with HELI PACK (5×5mm) and having an inner diameter of 20 mm and a height of 2 m, whole amount of the above-mentioned condensed liquid was fed from the upper portion of the column. Continuous distillation was carried out with a column liquid temperature of 135 ° C., a column top pressure of 10 mmHg and a reflux ratio of 2, the liquid having the composition comprising 6.52% by weight of dimethyl oxalate, 31.50% by weight of phenol and 61.95% by weight of methylphenyl oxalate was taken out from the top portion of the column with 43 ml/h, and diphenyl oxalate having the purity of 99.6% by weight was taken out from the bottom portion of the column with about 50g/h. The titanium concentration contained in the liquid taken out from the bottom portion of the column was measured by ICP, then, it was 2.5 ppm by weight.

In the obtained diphenyl oxalate, 20 ppm of benzofuran-2, 3-dione was contained as the furan compound, and a melt Hazen color index was 100.

Example 7

By using a distillation column made of a glass packed with HELI PACK (5×5 mm) and having an inner diameter of 20 mm and a height of 2 m, and, the bottom liquid of the column (diphenyl oxalate with a purity of 99.6% by weight) obtained in Example 6 was fed from the upper portion of the column with 100 ml/h. Continuous distillation was carried out with a colunm liquid temperature of 178° C., a column top pressure of 10 mmHg and a reflux ratio of 2, and the liquid having the composition comprising 99.9% by weight of diphenyl oxalate was taken out from the top portion of the column with about 98 g/h. From the bottom portion of the column, a liquid containing a high-boiling point material was taken out with about 7 g/h. The obtained diphenyl oxalate contained, as impurities, 0.02% by weight of phenol, 30 ppm of methylphenyl oxalate and 80 ppm of benzofuran-2,3-dione, and a melt Hazen color index was 100.

Example 8

Synthesis of Diphenyl Carbonate

To the diphenyl oxalate obtained in Example 6 was added 1.5 mol % of tetraphenylphosphonium chloride, and the mixture was dissolved by heating to 150° C. This liquid wsa fed with 300 mL/h to an apparatus in which two reactors made of a glass and equipped with a thermometer, a stirrer and an overflow tube (an inner volume of 1 L) had been connected by using a metering pump, and two reactors were heated by using mantle heaters and decarbonylation of diphenyl oxalate was carried out by maintaining at 230° C. Incidentally, the overflow position of each reactor was made 600 mL. The reaction mixture was purified by distillation under reduced pressure to obtain diphenyl carbonate.

Example 9

From the upper portion of Oldershaw of First reaction-distillation column, a mixed liquid comprising 61.4% by weight of phenol and 38.6% by weight of dimethyl oxalate was fed with 330 g/h, and the bottom liquid (phenol solution of TPT) taken out from the bottom portion of the reaction-distillation column for synthesizing a catalyst of Synthetic example 1 was also fed with 9 ml/h. The bottom flask was heated to 190° C., transesterification was carried out while the vapor from the top portion of the column was condensed with the condenser and taken out with the reflux ratio of 2. At the time (5 hours after starting feeding) at which the state of the column became stable, when the composition of the bottom liquid was analyzed by gas chromatography, it was 6.74% by weight of diphenyl oxalate, 26.76% by weight of methylphenyl oxalate, 23.45% by weight of dimethyl oxalate and 42.62% by weight of phenol. An amount of the bottom liquid taken out from the column was 306 g/h. From the top portion of the column, the liquid having the composition comprising 99.7% by weight of methanol and 0.3% by weight of dimethyl oxalate was taken out with about 24 g/h.

As Second reaction-distillation column, the same type of Oldershaw type reaction-distillation column as First reaction-distillation column was used, and to the 12$^{th}$ step from the top of Second reaction-distillation column was fed the reaction mixture after the above-mentioned transesterification with 300 ml/h. The bottom flask was heated by a mantle heater to 230° C., and disproportionation reaction was carried out while condensing the vapor from the top portion of the column by the condenser without reflux, and taking out of the system. At the time (5 hours after starting feeding) at which the state of the column became stable, when the composition of the bottom liquid was analyzed by gas chromatography, it was 53.22% by weight of diphenyl oxalate, 25.81% by weight of methylphenyl oxalate, 2.37% by weight of dimethyl oxalate and 17.14% by weight of phenol. An amount of the bottom liquid taken out from the column was about 132 g/h. From the top portion of the column, the liquid having the composition comprising 2.32% by weight of methanol, 43.75% by weight of dimethyl oxalate, 50.16% by weight of phenol, 3.64% by weight of methylphenyl oxalate and 0.13% by weight of diphenyl oxalate was taken out with about 189 g/h.

To the rotary thin film evaporator (heat transfer area: 0.1 m$^2$) the pressure of which had been reduced to 20 mmHg was fed the bottom liquid of the column (the reaction mixture) obtained above with 100 ml/h, and the evaporator was heated to 200° C. by a heating medium, dimethyl oxalate, phenol, methylphenyl oxalate and dimethyl oxalate were continuously evaporated and condensed by the condenser. From the bottom portion of the evaporator, the liquid containing about 20% by weight of tetraphenoxy titanium was taken out with about 7 g/h.

Incidentally, the piping from the vapor outlet of the thin film evaporator to the condenser was made a horizontal pipe, and no demister was provided.

Further, by using a distillation column made of a glass packed with HELI PACK (5×5 mm) and having an inner diameter of 20 mm and a height of 2 m, whole amount of the above-mentioned condensed liquid was fed from the upper portion of the column. Continuous distillation was carried out with a bottom temperature of 135° C., a column top pressure of 10 mmHg and a reflux ratio of 2, the liquid having the composition comprising 6.51% by weight of dimethyl oxalate, 31.57% by weight of phenol and 61.83% by weight of methylphenyl oxalate was taken out from the top portion of the column with 43 ml/h, and diphenyl oxalate having the purity of 99.5% by weight was taken out from the bottom portion of the column with about 50 g/h. The titanium concentration contained in the liquid taken out from the bottom portion of the column was measured by ICP, then, it was 38 ppm by weight.

In the obtained diaryl oxalate, 100 ppm of benzofuran-2,3-dione was contained as the furan compound, and a melt Hazen color index was 500.

Example 10

Distillation and purification were carried out in the same manner as in Example 7 except for using the bottom liquid of the column obtained in Example 9. From the top portion of the column, the liquid having the composition comprising 99.9% by weight of diphenyl oxalate was taken out with about 98 g/h. From the bottom portion of the column, a liquid containing a high-boiling point material was taken out with about 7 g/h. The obtained diphenyl oxalate contained, as impurities, 0.04% by weight of phenol, 30 ppm of methylphenyl oxalate and 760 ppm of benzofuran-2,3-dione, and a melt Hazen color index was 400.

Example 11

Between the distillation portion and the reaction portion of the distillation column of First reaction-distillation column, the mixed liquid comprising 50.4% by weight of phenol, 42.1% by weight of dimethyl oxalate, 3.2% by weight of methylphenyl oxalate, and others was fed with 261.5 kg/h, and the bottom liquid (phenol solution of TPT) taken out from the bottom portion of the reaction-distillation column for synthesizing a catalyst obtained in the same manner as in Synthetic example 1 was fed with 1.3 kg/h. While adjusting the pressure at the top portion of the column to 0.07 MPaG, the temperature of the bottom portion of the column was heated to 210° C. The vapor from the top portion of the column was condensed by the condenser and taken out with the reflux ratio of 4, and the bottom liquid of the column was continuously taken out so that the liquid amount could be maintained at a constant amount. At this time, the composition of the top liquid of the column was 98.4% by weight of methanol, 0.8% by weight of dimethyl oxalate, and others, and an amount taken out was 12.8 kg/h. The composition of the bottom liquid of the column was 27.5% by weight of dimethyl oxalate, 38.4% by weight of phenol, 26.5% by weight of methylphenyl oxalate, 5.6% by weight of diphenyl oxalate, and others, and an amount taken out was 250.0 kg/h.

As Second reaction-distillation column, a reaction-distillation column equipped with a plate portion was used, the bottom liquid of the column of First reaction-distillation column was fed to the top portion of the column of Second reaction-distillation column with 250.0 kg/h, and further, the top liquid of the column of Second distillation column which is a post-step was fed to the bottom portion of the column of Second reaction-distillation column with 28.4 kg/h, and while adjusting the pressure of the top portion of the column to 191 Ton, the temperature of the bottom portion of the column was heated to 200° C. Disproportionation reaction was carried out while condensing the vapor from the top portion of the column by the condenser and taking out whole amount thereof, and continuously taking out the bottom liquid of the column so that the liquid amount could be maintained at a constant amount. At this time, the composition of the top liquid of the column was 45.5% by weight of dimethyl oxalate, 49.7% by weight of phenol, 4.3% by weight of methylphenyl oxalate and others, and an amount taken out was 190.3 kg/h, which were recycled into First reaction-distillation column. An amount taken out from the bottom portion of the column was 88.1 kg/h, and the composition thereof was 62.5% by weight of diphenyl oxalate, 24.3% by weight of methylphenyl oxalate, 2.1% by weight of dimethyl oxalate, 5.2% by weight of phenol, and others.

The bottom liquid of the column of Second reaction-distillation column was fed to the falling film evaporator with 88.1 kg/h, and while adjusting the pressure to 23 Torr, the distillate was taken out with 74.9 kg/h. The composition thereof was 63.3% by weight of diphenyl oxalate e, 28.1% by weight of methylphenyl oxalate, 6.0% by weight of phenol, 2.4% by weight of dimethyl oxalate, and others. The composition of the column liquid contains 58.0% by weight of diphenyl oxalate, 2.5% by weight of methylphenyl oxalate, 10.0% by weight of tetraphenoxy titanium, and others, and among these, 1.0 kg/h thereof was purged, and the remaining 12.2 kg/h was recycled into First reaction-distillation column.

The distillate from the falling film evaporator was fed to First reaction-distillation column with 74.9 kg/h. While adjusting the pressure of the top portion of the column to 20 Torr, the temperature of the bottom liquid of the column was heated to 218° C. The vapor from the top portion of the column was condensed by the condenser and taken out with the reflux ratio of 0.5, and recycled into Second reaction-distillation column with 28.4 kg/h. The composition was 74.1% by weight of methylphenyl oxalate, 16.0% by weight of phenol, 6.4% by weight of dimethyl oxalate, 3.6% by weight of diphenyl oxalate, and others. An amount taken out from the bottom portion of the column was 46.5 kg/h, and the composition thereof was 99.8% by weight of diphenyl oxalate and others.

The bottom liquid of the column of First distillation column was fed to Second distillation column, and while adjusting the pressure of the top portion of the column to 15 Torr, the temperature of the bottom portion of the column was heated to 230° C. The vapor from the top portion of the column was condensed by the condenser and taken out with the reflux ratio of 5, and the bottom liquid of the column was continuously taken out so that the temperature became constant. At this time, the composition of the top liquid of the column was 99.9% by weight of diphenyl oxalate and others, and an amount taken out was 46.2 kg/h. An amount taken out from the bottom portion of the column was 0.3 kg/h, and the composition thereof was 75.9% by weight of diphenyl oxalate, and others.

In the above-mentioned apparatuses, i.e., the materials at the liquid-contacting portion of First reaction-distillation column, Second reaction-distillation column, the flowing film evaporator, First distillation column and Second distillation column were SUS316L. After 8000 hours (h), the inside thereof was subjected to surface observation (SEM) and structure inspection (SUMP), but abnormal portion which causes any problem was not observed in the respective portions.

<Evaluation 1>

In Example 11, test pieces of SUS316L were placed at the bottom portion of First reaction-distillation column, the bottom portion of Second reaction-distillation column, the bottom portion of First distillation column and the bottom portion of Second distillation column, and after 8000 hours lapsed, test pieces were taken out, and corrosion rates thereof were measured by the change in weight. The results are shown in Table 2.

TABLE 2

|  | Corrosion rate (mm/y) | Visual observation |
|---|---|---|
| Bottom portion of First reaction-distillation column | 0.006 | No corrosion |
| Bottom portion of Second reaction-distillation column | 0.004 | No corrosion |
| Bottom portion of First distillation column | 0.001 | No corrosion |
| Bottom portion of Second distillation column | 0.002 | No corrosion |

<Evaluation 2>

In Example 11, test pieces of SUS316 were placed at the bottom portion of First reaction-distillation column, the bottom portion of Second reaction-distillation column, the bottom portion of First distillation column and the bottom portion of Second distillation column, and after 8000 hours lapsed, test pieces were taken out, and corrosion rates thereof were measured by the change in weight. The results are shown in Table 3.

TABLE 3

|  | Corrosion rate (mm/y) | Visual observation |
|---|---|---|
| Bottom portion of First reaction-distillation column | 0.003 | No corrosion |
| Bottom portion of Second reaction-distillation column | 0.004 | No corrosion |
| Bottom portion of First distillation column | 0.002 | No corrosion |
| Bottom portion of Second distillation column | 0.003 | No corrosion |

<Evaluation 3>

In Example 11, test pieces of SUS304 were placed at the bottom portion of First reaction-distillation, the bottom portion of Second reaction-distillation column, the bottom portion of First distillation column and the bottom portion of Second distillation column, and after 8000 hours lapsed, test pieces were taken out, and corrosion rates thereof were measured by the change in weight. The results are shown in Table 4.

TABLE 4

|  | Corrosion rate (mm/y) | Visual observation |
|---|---|---|
| Bottom portion of First reaction-distillation column | 0.98 | Remarkable corrosion |
| Bottom portion of Second reaction-distillation column | 0.07 | No corrosion |
| Bottom portion of First distillation column | 0.03 | No corrosion |
| Bottom portion of Second distillation column | 0.34 | Corrosion exists |

<Evaluations 4 to 14>

At the bottom portion of First reaction-distillation column at which the corrosion rate was the highest in Evaluation 3, test pieces shown in Table 4 were provided, and after 8000 hours lapsed, each test piece was taken out, and appearance thereof was observed.

The test piece an appearance of which could be judged as the same results after the test of Evaluation 1 was evaluated to as "O", and the test piece an appearance of which would clearly be corroded than that after the test of Evaluation 1 was evaluated to as "X".

Chemical components of the steel materials used in Evaluations 4 to 14 are also shown in Table 5.

TABLE 5

|  | Kind of steel material | Chemical components of the steel material | | | | Appearance observation |
|---|---|---|---|---|---|---|
|  |  | Ni | Cr | Mo | N |  |
| Evaluation 4 | Carbon steel | — | — | — | — | X |
| Evaluation 5 | SUS201 | 3.50-5.50 | 16.00-18.00 | — | ≤0.25 | X |
| Evaluation 6 | SUS202 | 4.00-6.00 | 17.00-19.00 | — | ≤0.25 | X |
| Evaluation 7 | SUS301 | 6.00-8.00 | 16.00-18.00 | — | — | X |
| Evaluation 8 | SUS302B | 8.00-10.00 | 17.00-19.00 | — | — | X |
| Evaluation 9 | SUS303 | 8.00-10.00 | 17.00-19.00 | ≤0.6 | — | X |
| Evaluation 10 | SUS304 | 8.00-10.00 | 18.00-20.00 | — | — | X |
| Evaluation 11 | SUS304L | 9.00-13.00 | 18.00-20.00 | — | — | X |
| Evaluation 12 | SUS304N1 | 7.00-10.50 | 18.00-20.00 | — | 0.10-0.25 | X |
| Evaluation 13 | SUS304N2 | 18.00-20.00 | 18.00-20.00 | — | 0.15-0.30 | X |
| Evaluation 14 | SUS304LN | 8.50-11.50 | 17.00-19.00 | — | 0.12-0.22 | X |

Example 12

Synthesis of Diphenyl Carbonate

To diphenyl oxalate (purity: 99.9% by weight) obtained in Example 11 was added 1.5 mol % of tetraphenylphosphonium chloride, and the mixture was heated to 150° C. to dissolve the mixture. The liquid was fed to an apparatus in which two reactors (inner volume: 1 L) made of a glass and equipped with a thermometer, a stirrer and an overflow tube had been connected by using a metering pump with 300 mL/h, and two reactors were heated by mantle heaters to maintain the mixture at 230° C. to carry out decarbonylation reaction of the diphenyl oxalate. An overflow position of the respective reactors was made each 600 mL. The reaction mixture was purified by distillation under reduced pressure to obtain diphenyl carbonate.

Example 13

Synthesis of Polycarbonate Resin

Bisphenol A and diphenyl carbonate obtained in Example 12 were mixed with a molar ratio of 1:1.07, and maintained at 130° C. for 24 hours to obtain a mixed melt.

To the obtained mixed melt was added 0.01N sodium hydroxide as a catalyst in an amount of 1 μmol based on 1 mol of bisphenol A under nitrogen atmosphere, and polycondensation reaction was carried out at 210° C./100 mmHg for 60 minutes, at 240° C./15 mmHg for 60 minutes and at 280° C./0.5 mmHg for 2 hours, while removing the by-producing phenol at any time to obtain an aromatic polycarbonate having a viscosity average molecular weight of 20,000.

Example 14

[Step (A)]

To a reactor made of a stainless comprising an inner diameter of 27.1 mm and a height of 500 mm tube was packed a solid catalyst in which 0.5% by weight of palladium was carried on a pellet-shaped a-alumina having a diameter of 5 mm and a length of 3 mm. Hot water was passed through the shell side of the reactor to maintain the temperature of the catalyst layer to 100° C. or so, and then, the starting gas (Composition: 22.0% by volume of carbon monoxide, 10.0% by volume of methyl nitrite, 4.0% by volume of nitrogen monoxide, 5.2% by volume of methanol, 1.7% by volume of carbon dioxide and 57.1% by volume of nitrogen) was fed thereto with 1.15 $Nm^3$/h and 0.2 MpaG to prepare dimethyl oxalate.

The gas passed through the catalyst layer was led to the bottom of the column of the gas-liquid contact absorber having an inner diameter of 43 mm and a height of 1000 mm, and it was countercurrent-contacted with 0.42 L/h of methanol introduced therein from the top of the column at about 35° C. (column top temperature of 30° C., column bottom temperature of 40° C.). Then, 0.3 kg/h of a condensed liquid (Composition: 42.6% by weight of dimethyl oxalate, 1.8% by weight of dimethyl carbonate, 0.03% by weight of methyl formate and 42.6% by weight of methanol) was obtained from the bottom of the column, and 1.23 $Nm^3$/h of a non-condensed gas (Composition:

16.2% by volume of carbon monoxide, 4.9% by volume of methyl nitrite, 8.1% by volume of nitrogen monoxide, 15.9% by volume of methanol, 1.8% by volume of carbon dioxide and 53.1% by volume of nitrogen) was obtained from the top of the column.

A gas in which 13.8 NL/h of oxygen and 0.5 NL/h of nitrogen monoxide were mixed with the non-condensed gas was led to the bottom of the column of the gas-liquid contact type regenerator having an inner diameter of 83 mm and a height of 1000 mm, and was countercurrent-conatcted with 0.33 L/h of methanol introduced therein from the top of the column, so that the nitrogen monoxide in the gas was regenerated to methyl nitrite. To the reactor were fed 1.1 $Nm^3$/h (2.1 $kg/cm^2$G) of the regenerated gas (Composition: 18.2% by volume of carbon monoxide, 10.4% by volume of methyl nitrite, 4.2% by volume of nitrogen monoxide, 5.4% by volume of methanol, 2.0% by volume of carbon dioxide and 53.0% by volume of nitrogen) led out from the top of the column of the regenerator and 49 NL/h (2.1 $kg/cm^2$G) of carbon monoxide.

Since 0.48 L/h of methanol containing 5.7% by weight of water and led out from the bottom of the column of the regenerator contains a small amount of nitric acid, so that it was reused as a methanol source in the regenerator after neutralizing it with caustic soda, and removing water by distillation.

On the other hand, the condensed liquid stored for 50 hours was subjected to batch distillation in a distillation column (a volume at the bottom portion of the column: 100L) having an inner diameter of 150 nun and a height of 7500 mm As a result, 5.8 kg of dimethyl oxalate having a purity of 99.9% by weight was obtained.

[Step (B-1)]

By using the dimethyl oxalate obtained in Step (A), diphenyl oxalate was prepared as follows.

From the upper portion of First reaction-distillation column, a mixed liquid comprising 54.5% by weight of phenol and 45.5% by weight of dimethyl oxalate was fed with 600 ml/h, and the bottom liquid (phenol solution of TPT) taken out from the bottom portion of the reaction-distillation column for synthesizing a catalyst obtained in the same manner as in Synthetic example 1 was fed with 18 ml/h. The bottom portion of the column of First reaction-distillation column was heated to 190° C., and trans-esterification was carried out while condensing the vapor from the top portion of the column by the condenser and taking it out with the reflux ratio of 2.

At the time (4 hours after starting feeding) at which the state of the column became stable, when the composition of the bottom liquid of the column was 6.23% by weight of diphenyl oxalate, 29.95% by weight of methylphenyl oxalate, 23.88% by weight of dimethyl oxalate and 39.41% by weight of phenol, and an amount taken out thereof was about 603 g/h. Also, at this time, the liquid having the composition comprising 98.0% by weight of methanol, 0.9% by weight of dimethyl oxalate and 1.1% by weight of anisole was taken out from the top of the column with about 44 g/h.

[Step (B-2)]

The bottom liquid of the column (the bottom liquid of the column of First reaction-distillation column) by the transcsterification was fed from the upper portion of Second reaction-distillation column which is the same shape as First reaction-distillation column under reduced pressure of 200 mmHg with 600 ml/h, and the bottom of the column of Second reaction-distillation column was heated to 200° C. and the vapor from the top portion of the column was cooled to carry out to the disproportionation reaction.

At the time (4 hours after starting feeding) at which the state of the column became stable, the composition of the bottom liquid of the column was 65.27% by weight of diphenyl oxalate, 18.43% by weight of methylphenyl oxalate, 1.02% by weight of dimethyl oxalate and 13.93% by weight of phenol, and an amount taken out thereof was about 252 g/h. Also, at this time, the liquid having the composition comprising 1.57% by weight of methanol, 2.97% by weight of dimethyl oxalate, 48.51% by weight of phenol, 2.97% by weight of methylphenyl oxalate and 0.42% by weight of diphenyl oxalate was taken out from the top of the column with about 355 g/h.

[Step (B-3)]

The bottom liquid of the column (the bottom liquid of the column of Second reaction-distillation column) after the disproportionation reaction was fed to the thin film evaporator, and dimethyl oxalate, phenol, methylphenyl oxalate and diphenyl oxalate were continuously evaporated. The obtained vapor was fed to the distillation column to carry out continuous distillation. Then, from the top portion of the column of the distillation column, the liquid having the composition comprising 3.05% by weight of dimethyl oxalate, 41.73% by weight of phenol and 55.21% by weight of methylphenyl oxalate was taken out with about 68 ml/h, and from the bottom portion of the column of the distillation column, diphenyl oxalate having the purity of 99.7% by weight was taken out with about 120 g/h. Also, from the bottom portion of the evaporator, the liquid containing about 2.5% by weight (in terms of a metal) of titanium was taken out with about 14 g/h.

[Step (C)]

Purification of methanol was carried out by using the distillate (Composition: 98.0% by weight of methanol, 0.9% by weight of dimethyl oxalate and 1.1% by weight of anisole) taken out from the top of the column in the transesterification of dimethyl oxalate and phenol in Step (B-1) and using the Oldershaw used in Step (B-1). When the purification was carried out by the distillation conditions of a normal pressure and the reflux ratio of 1, then, the fractions obtained from the top of the column was methanol containing a detection limit or less (1 ppm or less) of dimethyl oxalate and 18 ppm of anisole.

[Utilization of Recovered Methanol for Step (A)]

By using the recovered methanol obtained in Step (C), preparation of the dimethyl oxalate was carried out in the same manner as in Example 14. From Step (A) to Step (B-3), completely the similar results as in Example 14 could be obtained.

Example 15

In a round bottom flask having a volume of 300 ml and equipped with a thermometer and a stirrer were charged 200 g of diphenyl oxalate obtained in Example 14 and 1.55 g of tetraphenylphosphonium chloride, and heated by a mantle heater to carry out decarbonylation reaction at 250° C. for 2 hours. During the reaction, the generating carbon monoxide was discharged from an exhausting tube connected with the reactor to outside of the system. When the composition of the reaction mixture in the reactor was analyzed by gas chromatography, it was 98.1% by weight of diphenyl carbonate and 1.1% by weight of diphenyl oxalate.

In this state, the solution in which 0.5 mol % of tetraphenylphosphonium chloride was dissolved in the diphenyl oxalate obtained in Example 1 was fed to the reactor with 70 ml/h, and the reaction mixture was continuously taken out so that its volume was maintained to 200 ml. Also, the temperature in the reactor was controlled to maintain 250° C. by the mantle heater. At the time (about 10 hours after starting the continuous reaction) at which the composition of the reaction mixture became stable, when the taken out liquid was analyzed, it was 91.2% by weight of diphenyl carbonate and 7.8% by weight diphenyl oxalate. Also, from the reactor, carbon monoxide was generated with about 110 ml/h, and its purity was substantially 100%.

Example 16

Preparation of dimethyl oxalate was carried out in the same manner as in Example 1 by using the distillate (Composition: 98.0% by weight of methanol, 0.9% by weight of dimethyl oxalate and 1.1% by weight of anisole) taken out from the top of the column in the transesterification of dimethyl oxalate and phenol in Example 15. At the initial stage, completely the similar results could be obtained from Step A to Step B-3 in Example 14, but the reaction yield showed the tendency of gradually lowering with a lapse of time.

Examples 17 to 19

To examine the effect of anisole in the dimethyl oxalate reaction step, synthesis of dimethyl oxalate was carried out by using the jacketed reactor made of SUS having an inner diameter of 20 mm. In the reactor was packed 5 ml of the pellet-shaped solid catalyst same as in Example 14, while controlling the temperature of the catalyst layer to 120° C. by passing a heat medium through the jacket, a mixed gas comprising 22.0% by volume of carbon monoxide, 10.0% by volume of methyl nitrite, 4.0% by volume of nitrogen monoxide, 6.2% by volume of methanol and 57.8% by volume of nitrogen was fed to the reactor with 22 NL/h and 0.2 MpaG to synthesize dimethyl oxalate. Also, to examine the effect of the anisole to the reaction, a predetermined amount of the anisole was added to the mixed gas and the mixed gas was fed to the reactor to carry out synthesis of dimethyl oxalate. The results are shown below. In Table 6, Activity lowering rate is an STY lowering rate per 1,000 hours.

TABLE 6

| Example | Anisole added amount | Dimethyl oxalate STY | Selectivity based on CO | Activity lowering rate |
|---------|---------------------|---------------------|------------------------|----------------------|
| 17 | 0 ppm | 1,000 g/lh | 98.9% | 10% |
| 18 | 1,000 ppm | 990 g/lh | 98.5% | 40% |
| 19 | 100 ppm | 1,000 g/lh | 98.6% | 10% |

STY in Table 6 is a Space Time Yield, and represents a yield per unit volume of the reaction apparatus, and per a unit time.

From the results shown in Table 6, it can be understood that when the ether content in the alkyl alcohol removed in the alkylaryl oxalate-forming Step (B-1) is 1000 ppm by weight or higher, the catalyst activity is lowered and lifetime of the catalyst is shortened in Step (A) where the alkyl alcohol is used by recycling.

The invention claimed is:

1. A process for preparing a diaryl oxalate which comprises steps of:
    reacting a tetraalkoxy titanium and an excess amount of an aryl alcohol and removing a by-producing alkyl alcohol to obtain an aryl alcohol solution of a tetra(aryloxy) titanium;
    thereafter feeding the obtained aryl alcohol solution of a tetra(aryloxy)titanium in a reaction system of transesterification as a catalyst of the transesterification;
    transesterifying, in the reaction system, an alkylaryl oxalate with an aryl alcohol in the presence of the catalyst to prepare the diaryl oxalate; and
    making a concentration of a titanium compound of a reaction mixture containing the diaryl oxalate 10 ppm by weight or less, and then, purifying by distillation, in order to obtain a diaryl oxalate with 500 ppm or less benzofuran-2,3-diones as a coloring component, wherein a material of an apparatus contacting with a reaction solution of the transesterification is an austenitic stainless steel containing 10% by weight or more of nickel and 1 to 4% by weight of molybdenum, or containing 16.00 to 18.00% by weight of chromium; and wherein the material of an apparatus is an austenitic stainless steel substantially not containing a nitrogen atom.

2. The process for preparing diaryl oxalate according to claim 1, wherein the tetra(aryloxy)titanium is tetraphenoxy titanium.

3. The process for preparing diaryl oxalate according to claim 1, wherein the tetraalkoxy titanium is tetraisopropoxy titanium.

4. The process for preparing diaryl oxalate according to claim 1, wherein the reaction of the tetraalkoxy titanium and an excess amount of the aryl alcohol is carried out so that a molar ratio (aryl alcohol/titanium atom) of the aryl alcohol and a titanium atom in the tetraalkoxy titanium becomes 10 to 80.

5. The process for preparing diaryl oxalate according to claim 1, wherein the reaction of the tetraalkoxy titanium and an excess amount of the aryl alcohol is carried out while maintaining a reaction temperature at 160 to 300° C.

6. The process for preparing diaryl oxalate according to claim 1, wherein the reaction of the tetraalkoxy titanium and an excess amount of the aryl alcohol is carried out in a reaction-distillation column.

7. The process for preparing diaryl oxalate according to claim 6, wherein a reflux ratio of the tetraalkoxy titanium and an excess amount of the aryl alcohol in the reaction-distillation column is 3 to 40.

8. The process for preparing diaryl oxalate according to claim 6, wherein the tetraalkoxy titanium and an excess amount of the aryl alcohol are continuously fed to the reaction-distillation column so that a molar ratio (aryl alcohol/titanium atom) of the aryl alcohol and a titanium atom in the tetraalkoxy titanium per a unit time becomes 40 to 80.

9. The process for preparing diaryl oxalate according to claim 1, wherein the tetraalkoxy titanium and an excess amount of the aryl alcohol are fed to a reaction-distillation column to carry out a reaction, a fraction containing a by-producing alkyl alcohol is taken out by distillation, and a fraction containing the tetra(aryloxy)titanium and the aryl alcohol is taken out from a bottom portion, to obtain an aryl alcohol solution of the tetra(aryloxy)titanium from which the by-producing alkyl alcohol had been removed, and fed the same to a transesterification step.

10. The process for preparing diaryl oxalate according to claim 9, wherein the tetra(aryloxy)titanium and the aryl alcohol are continuously taken out from a bottom portion of the reaction-distillation column, and the aryl alcohol solution of the tetra(aryloxy)titanium from which the by-producing alkyl alcohol had been removed is continuously fed to the transesterification step.

11. The process for preparing diaryl oxalate according to Claim 1, wherein a material of an apparatus is a SUS316 series austenitic stainless steel regulated by JIS G 4304.

12. The process for preparing diaryl oxalate according to claim 11, wherein the austenitic stainless steel is SUS316 or SUS316L regulated by JIS G 4304.

13. The process for preparing diaryl oxalate according to claim 1, wherein an apparatus is a purification column of the diaryl oxalate, a reaction apparatus of transesterification or a reaction-distillation column.

14. A process for preparing diaryl carbonate which comprises decarbonylating the diaryl oxalate prepared by the process according to claim 1 in the presence of a phosphorus compound.

15. A process for preparing polycarbonate which comprises reacting diaryl carbonate prepared by the process according to claim 14 with bisphenol A in the presence of a basic alkali metal salt.

* * * * *